(12) United States Patent
Hasik et al.

(10) Patent No.: US 12,017,244 B2
(45) Date of Patent: Jun. 25, 2024

(54) VOLATILE MATERIAL DISPENSER

(71) Applicant: S. C. Johnson & Son, Inc., Racine, WI (US)

(72) Inventors: Sebastian D. Hasik, Antioch, IL (US); Gregory G. Pieper, Spring Grove, IL (US); Katherine Cusatis, Wauwatosa, WI (US); James T. Walker, Racine, WI (US); Brian T. Davis, Burlington, WI (US); Timothy R. Ordiway, Racine, WI (US)

(73) Assignee: S. C. JOHNSON & SON, INC., Racine, WI (US)

( * ) Notice: Subject to any disclaimer, the term of this patent is extended or adjusted under 35 U.S.C. 154(b) by 0 days.

(21) Appl. No.: 17/844,579

(22) Filed: Jun. 20, 2022

(65) Prior Publication Data

US 2022/0314262 A1    Oct. 6, 2022

Related U.S. Application Data

(62) Division of application No. 16/579,489, filed on Sep. 23, 2019, now Pat. No. 11,407,000.

(51) Int. Cl.
*B05B 17/06*      (2006.01)
*B05B 17/00*      (2006.01)
*F21S 10/02*      (2006.01)

(52) U.S. Cl.
CPC ...... *B05B 17/0646* (2013.01); *B05B 17/0684* (2013.01); *F21S 10/02* (2013.01)

(58) Field of Classification Search
CPC .................. B05B 17/0684; B05B 17/0646
See application file for complete search history.

(56) References Cited

U.S. PATENT DOCUMENTS 3,970,250 A    7/1976    Drews
D241,918 S    10/1976    Knickerbocker
(Continued)

FOREIGN PATENT DOCUMENTS

AU    327391 S    8/2009
AU    360406 S    2/2015
(Continued)

OTHER PUBLICATIONS

Invitation to Pay Additional Fees and Communication Relating to Results of Partial International Search Report from corresponding PCT Application No. PCT/US2020/050703 dated Nov. 24, 2020 (13 pages).

*Primary Examiner* — Qingzhang Zhou
(74) *Attorney, Agent, or Firm* — Quarles & Brady LLP

(57) ABSTRACT

A volatile material dispenser includes a base that houses a printed circuit board. The volatile material dispenser also includes a stand assembly and a shroud. The stand assembly is coupled with the base. The stand assembly includes a platform, a stand that extends from the platform, and a manifold that extends from the stand. The manifold contains a circular piezoelectric element. The shroud is positioned on the base. The shroud defines a chimney that is centered along a longitudinal axis. The manifold includes an annular wall that extends from the manifold. A spring is disposed within the manifold and is coaxial with the annular wall. A top end of the spring is wrapped around the annular wall and a bottom end of the spring applies a force against the piezoelectric element.

14 Claims, 24 Drawing Sheets

(56) References Cited

U.S. PATENT DOCUMENTS

| | | |
|---|---|---|
| D310,723 S | 9/1990 | Su |
| 6,269,976 B1 | 8/2001 | DeJonge |
| 6,290,103 B1 | 9/2001 | Fraillon |
| 6,296,196 B1 | 10/2001 | Denen et al. |
| 6,382,522 B2 | 5/2002 | Tomkins et al. |
| 6,386,462 B1 | 5/2002 | Martens, III |
| 6,786,427 B2 | 9/2004 | Schram et al. |
| 6,899,280 B2 | 5/2005 | Kotary et al. |
| 7,007,863 B2 | 3/2006 | Kotary et al. |
| 7,032,831 B2 | 4/2006 | Duston et al. |
| D532,301 S | 11/2006 | Moretti |
| 7,244,398 B2 | 7/2007 | Kotary et al. |
| D553,499 S | 10/2007 | Lavelli |
| 7,281,670 B2 | 10/2007 | Lakatos et al. |
| D555,004 S | 11/2007 | Nukuto et al. |
| 7,303,143 B2 | 12/2007 | Davis et al. |
| 7,309,024 B2 | 12/2007 | Hansen et al. |
| 7,455,245 B2 | 11/2008 | Sipinski et al. |
| D583,678 S | 12/2008 | Yamamoto |
| 7,538,473 B2 | 5/2009 | Blandino et al. |
| 7,540,473 B2 | 6/2009 | Schwarz |
| D596,939 S | 7/2009 | Moretti |
| 7,610,118 B2 | 10/2009 | Schramm et al. |
| 7,622,073 B2 | 11/2009 | Schramm et al. |
| 7,757,902 B2 | 7/2010 | Bevans et al. |
| 7,775,459 B2 * | 8/2010 | Martens, III ........ B05B 17/0684 128/200.14 |
| D628,066 S | 11/2010 | Costa Quintas |
| 7,837,065 B2 | 11/2010 | Furner et al. |
| 7,932,482 B2 | 4/2011 | Norwood et al. |
| 7,954,667 B2 | 6/2011 | Furner et al. |
| D643,737 S | 8/2011 | Handy |
| D646,572 S | 10/2011 | Koeleman |
| 8,061,562 B2 | 11/2011 | Carpenter et al. |
| 8,061,567 B2 | 11/2011 | Bevans et al. |
| D651,086 S | 12/2011 | Gullickson et al. |
| 8,091,734 B2 | 1/2012 | Furner et al. |
| 8,135,265 B2 | 3/2012 | Tollens et al. |
| 8,157,188 B2 | 4/2012 | Duston et al. |
| D671,004 S | 11/2012 | Kelly et al. |
| 8,342,363 B2 | 1/2013 | Carpenter et al. |
| D679,607 S | 4/2013 | Park et al. |
| D680,443 S | 4/2013 | You |
| D680,444 S | 4/2013 | Park et al. |
| D681,475 S | 5/2013 | Park |
| 8,480,248 B2 | 7/2013 | Demarest et al. |
| 8,483,553 B2 | 7/2013 | Tollens et al. |
| D688,138 S | 8/2013 | Kim |
| 8,540,169 B2 | 9/2013 | Kambayashi et al. |
| 8,636,039 B2 | 1/2014 | Litten et al. |
| 8,657,160 B2 | 2/2014 | Lashells et al. |
| 8,678,233 B2 | 3/2014 | Furner et al. |
| D705,660 S | 5/2014 | Colloud |
| 8,733,670 B2 | 5/2014 | Lakatos et al. |
| D707,133 S | 6/2014 | In |
| 8,746,505 B2 | 6/2014 | Demarest et al. |
| 8,758,606 B2 | 6/2014 | Tranchant et al. |
| 8,887,954 B2 | 11/2014 | Carpenter et al. |
| 8,955,765 B2 | 2/2015 | Porchia et al. |
| D729,569 S | 5/2015 | Herbst et al. |
| 9,101,676 B2 | 8/2015 | Hoppe et al. |
| D758,206 S | 6/2016 | Hoeke et al. |
| D758,877 S | 6/2016 | Vaughn-Batiz |
| 9,393,334 B2 | 7/2016 | Litten-Brown et al. |
| 9,434,530 B2 | 9/2016 | Cornwell |
| 9,457,951 B2 | 10/2016 | Carpenter et al. |
| D781,150 S | 3/2017 | Zoppas |
| 9,586,228 B2 | 3/2017 | Roemburg et al. |
| 9,604,242 B2 | 3/2017 | Hess et al. |
| 9,636,430 B2 | 5/2017 | Gruenbacher et al. |
| D794,450 S | 8/2017 | Moreaux |
| D804,951 S | 12/2017 | Broen et al. |
| D806,568 S | 1/2018 | Chen et al. |
| D811,889 S | 3/2018 | Cheng |
| D815,908 S | 4/2018 | Kauss et al. |
| D817,095 S | 5/2018 | Kauss et al. |
| D817,096 S | 5/2018 | Kauss et al. |
| D821,201 S | 6/2018 | Harris et al. |
| D821,203 S | 6/2018 | Prater et al. |
| D821,205 S | 6/2018 | Christianson et al. |
| D821,877 S | 7/2018 | Harris et al. |
| 10,011,419 B2 | 7/2018 | Carpenter et al. |
| 10,040,083 B2 | 8/2018 | Barenhoff et al. |
| D831,482 S | 10/2018 | Meyers |
| 10,143,768 B2 | 12/2018 | Roemburg et al. |
| 10,232,393 B2 | 3/2019 | Dumont et al. |
| D846,397 S | 4/2019 | Prater et al. |
| 10,610,611 B2 | 4/2020 | Salowitz et al. |
| 10,702,884 B2 | 7/2020 | Beaumont et al. |
| 10,780,192 B2 | 9/2020 | Gruenbacher et al. |
| 2007/0056914 A1 | 3/2007 | Slager |
| 2008/0011874 A1* | 1/2008 | Munagavalasa .... B05B 17/0646 239/326 |
| 2010/0284168 A1 | 11/2010 | Walter et al. |
| 2011/0042481 A1 | 2/2011 | Kanamori |
| 2013/0079733 A1 | 3/2013 | Burt |
| 2017/0056914 A1 | 3/2017 | Beaumont |
| 2017/0165392 A1 | 6/2017 | Sevy |
| 2017/0341849 A1 | 11/2017 | Wolak et al. |
| 2018/0099806 A1 | 4/2018 | Li |
| 2019/0118210 A1 | 4/2019 | Freeman |
| 2019/0177147 A1 | 6/2019 | Harris et al. |
| 2019/0192717 A1 | 6/2019 | Harwig et al. |

FOREIGN PATENT DOCUMENTS

| | | |
|---|---|---|
| CA | 158743 S | 11/1914 |
| CA | 160735 S | 2/1915 |
| CA | 2680448 C | 9/2008 |
| CA | 303245831 S | 6/2015 |
| CA | 2997276 C | 3/2017 |
| CA | 3007941 A1 | 6/2017 |
| CN | 101258003 * | 9/2008 |
| CN | 303254324 S | 6/2015 |
| CN | 303305455 S | 7/2015 |
| CN | 304673365 S | 6/2018 |
| EM | 000063441-0003 | 8/2003 |
| EM | 000063441-0004 | 8/2003 |
| EM | 000277660-0001 | 1/2005 |
| EM | 000320411-0004 | 4/2005 |
| EM | 000668785-0001 | 5/2007 |
| EM | 000758743-0014 | 7/2007 |
| EM | 000758743-0015 | 7/2007 |
| EM | 000758743-0018 | 7/2007 |
| EM | 000758743-0022 | 7/2007 |
| EM | 000758743-0023 | 7/2007 |
| EM | 000758743-0024 | 7/2007 |
| EM | 001765702-0001 | 10/2010 |
| EM | 002072769-0008 | 7/2012 |
| EM | 002072769-0009 | 7/2012 |
| EM | 002072769-0010 | 7/2012 |
| EM | 002072769-0011 | 7/2012 |
| EM | 002419796-0001 | 3/2014 |
| EM | 002419796-0002 | 3/2014 |
| EM | 002485771-0001 | 6/2014 |
| EM | 002511758-0003 | 7/2014 |
| EM | 002677765-0002 | 4/2015 |
| EM | 002696310-0003 | 5/2015 |
| EM | 002696310-0010 | 5/2015 |
| EM | 002696310-0029 | 5/2015 |
| EM | 002696310-0035 | 5/2015 |
| EM | 002696310-0036 | 5/2015 |
| EM | 002696310-0045 | 5/2015 |
| EM | 002738773-0003 | 7/2015 |
| EM | 003037092-0001 | 3/2016 |
| EM | 003037092-0004 | 3/2016 |
| EM | 003763689-0001 | 2/2017 |
| EM | 003849975-0001 | 4/2017 |
| EM | 003849975-0002 | 4/2017 |
| EM | 003850718-0001 | 4/2017 |
| EM | 003850718-0002 | 4/2017 |
| EM | 004111185-0001 | 7/2017 |
| EM | 004245678-0007 | 9/2017 |
| EM | 004245678-0008 | 9/2017 |

(56) References Cited

FOREIGN PATENT DOCUMENTS

| | | |
|---|---|---|
| EM | 004245678-0011 | 9/2017 |
| EM | 004421287-0001 | 10/2017 |
| EM | 004549251-0001 | 12/2017 |
| EM | 004549251-0002 | 12/2017 |
| EM | 0059409050-0001 | 12/2018 |
| EM | 006630851-0001 | 7/2019 |
| EM | 006657318-0002 | 7/2019 |
| EP | 1651280 B1 | 9/2007 |
| EP | 1651280 B8 | 11/2007 |
| EP | 1807322 B1 | 1/2008 |
| EP | 1832526 B1 | 12/2008 |
| EP | 1952059 B1 | 7/2009 |
| EP | 1954407 B1 | 12/2009 |
| EP | 1613363 B1 | 10/2010 |
| EP | 1613362 B1 | 12/2010 |
| EP | 1549139 B1 | 11/2011 |
| EP | 2509890 A1 | 10/2012 |
| EP | 2384771 B1 | 1/2013 |
| EP | 2320959 B1 | 6/2014 |
| EP | 2842641 A1 | 3/2015 |
| EP | 1988933 B1 | 4/2015 |
| EP | 2054167 B1 | 4/2015 |
| EP | 2301332 B1 | 3/2017 |
| EP | 3142713 A2 | 3/2017 |
| EP | 2079647 B1 | 5/2017 |
| EP | 2841208 B1 | 2/2018 |
| EP | 3325022 A1 | 5/2018 |
| EP | 3349806 A1 | 7/2018 |
| EP | 3386553 A1 | 10/2018 |
| EP | 2004334 B1 | 11/2018 |
| EP | 2465791 B1 | 4/2020 |
| EP | 3684518 A1 | 7/2020 |
| EP | 3727480 A2 | 10/2020 |
| EP | 3756696 A1 | 12/2020 |
| JP | 1540071 S | 12/2015 |
| JP | 1540239 S | 12/2015 |
| JP | 1540816 S | 12/2015 |
| RU | 96719 U1 | 8/2010 |
| WO | DM/037 645 | 9/1996 |
| WO | 2004010762 A2 | 2/2004 |
| WO | DM/048 054 | 5/2004 |
| WO | 2006004891 A1 | 1/2006 |
| WO | 2008035303 A2 | 3/2008 |
| WO | 2009002430 A1 | 12/2008 |
| WO | DM/075 647 | 3/2011 |
| WO | DM/072 713 | 11/2014 |
| WO | 2015117625 A1 | 8/2015 |
| WO | DM/074 610 | 10/2015 |
| WO | 2015175527 A2 | 11/2015 |
| WO | 2017015273 A1 | 1/2017 |
| WO | 2017048663 A1 | 3/2017 |
| WO | 2017048665 A1 | 3/2017 |
| WO | 2017048666 A1 | 3/2017 |
| WO | 2017100070 A1 | 6/2017 |
| WO | DM/087 159 | 10/2017 |
| WO | 2017205199 A1 | 11/2017 |
| WO | 2019060441 A1 | 3/2019 |
| WO | 2019113447 A1 | 6/2019 |
| WO | 2019125805 A2 | 6/2019 |

* cited by examiner

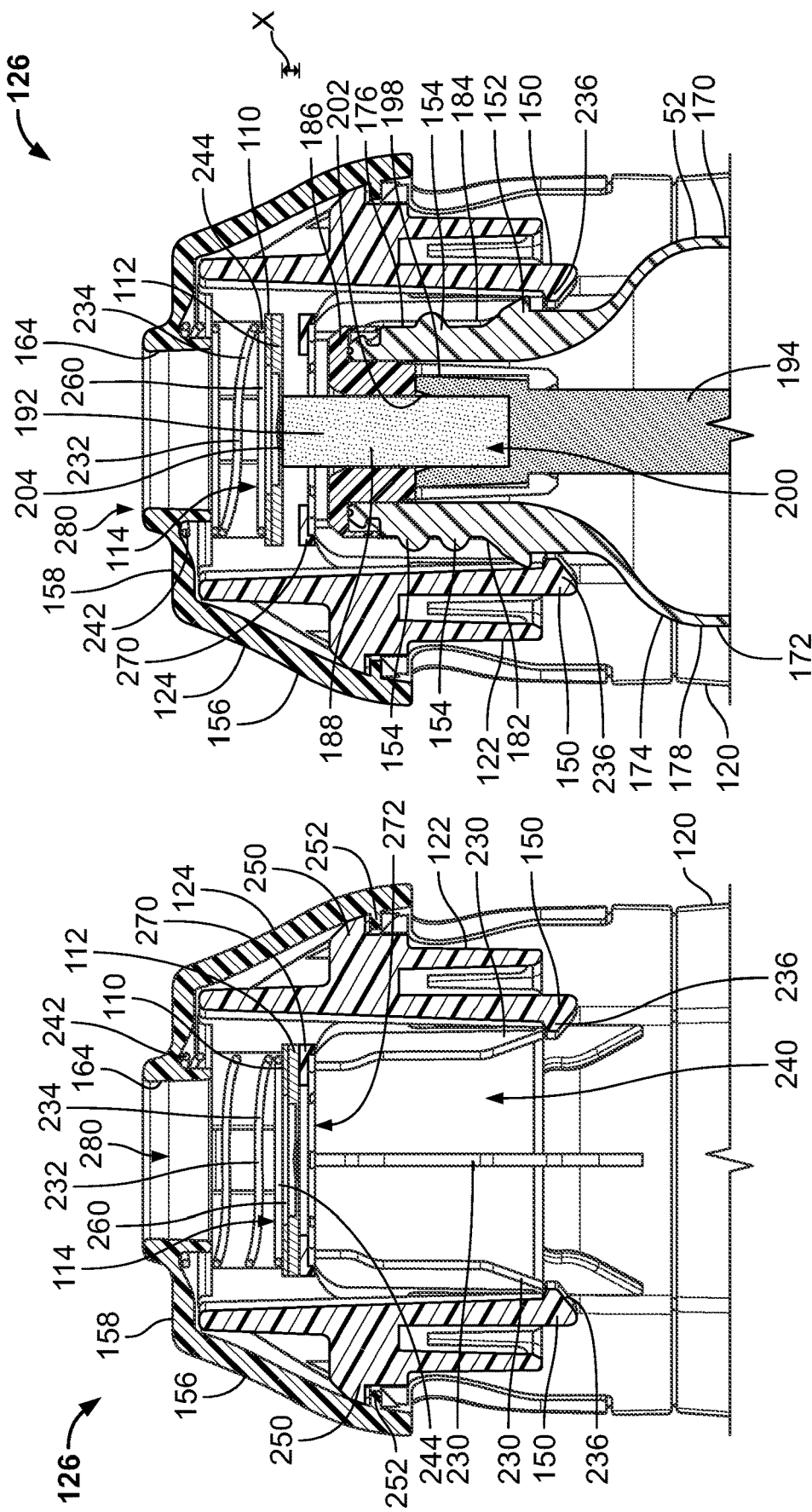

VOLATILE MATERIAL DISPENSER

CROSS REFERENCE TO RELATED APPLICATIONS

This application is a divisional of U.S. application Ser. No. 16/579,489, filed on Sep. 23, 2019, which is hereby incorporated by reference herein in its entirety.

BACKGROUND OF THE DISCLOSURE

1. Field of the Disclosure

The present disclosure relates generally to volatile material dispensers for emitting volatile materials and, more particularly, to volatile material dispensers having a piezoelectric element and lighting assembly.

2. Description of the Background of the Disclosure

Various volatile material dispensers are known in the art, most of which deliver fragrance to the surrounding environment by a variety of different mechanisms. For example, some dispensers spray a volatile containing a fragrance into the surrounding environment, while other dispensers allow for the evaporation of a volatile containing a fragrance into the surrounding environment. Such volatile material dispensers generally include a housing with a refill inserted therein. The refill generally includes a container for holding a volatile material, and the volatile material may include various components such as aroma chemicals, water, solvents, surfactants, alcohols, and/or other components. Some refills include a wick in contact with the volatile material and extending out of the refill to carry the volatile material out of the refill. Other refills include a gel-like substance that is emitted through a semi-permeable membrane. Regardless of the type of refill, the refill may be inserted into a volatile material dispenser having a heater, a piezoelectric element, an aerosol actuator, and/or any other diffusion element that may assist in delivering the volatile material.

However, many prior art dispensers do not distribute volatile materials in a uniform or accurately dosed fashion. Further, many dispensers fail to include visual feedback to a user regarding the amount or quantity of volatile that is being or has been dispensed by the volatile material dispenser. As such, there is a need for a volatile material dispenser having a mechanism that accurately disperses a volatile while providing adjustable, visual feedback to a user.

SUMMARY OF THE INVENTION

According to a first aspect, a volatile material dispenser comprises a base that houses a printed circuit board. The volatile material dispenser also comprises a stand assembly that is coupled with the base. The stand assembly includes a platform, a stand that extends from the platform, and a manifold that extends from the stand. The manifold contains a circular piezoelectric element. The volatile material dispenser further comprises a shroud positioned on the base. The shroud defines a chimney that is centered along a longitudinal axis. The manifold includes an annular wall that extends from the manifold. A spring is disposed within the manifold and is coaxial with the annular wall. A top end of the spring is wrapped around the annular wall and a bottom end of the spring applies a force against the piezoelectric element.

According to some embodiments, the spring has a spring wire with a diameter of between about 0.50 mm and about 0.60 mm. In some embodiments, the diameter of the spring wire is about 0.55 mm. In some embodiments, the volatile material dispenser further comprises a fan. In some embodiments, the volatile material dispenser further comprises a refill that includes a wick, and the refill is removably coupled with the manifold. In some embodiments, the spring causes a force to be exerted against the wick of the refill when the refill is inserted into the manifold. In some embodiments, the annular wall extends entirely around the longitudinal axis. In some embodiments, the manifold defines a refill cavity, and a plurality of refill retaining ribs extend from the manifold into the refill cavity. In some embodiments, the manifold comprises a chassis and a crown that is snap fit to the chassis.

According to another aspect, a volatile material dispenser comprises a base that houses a printed circuit board. The volatile material dispenser also comprises a stand assembly that is coupled with the base. The base comprises a plurality of light emitting diodes. The stand assembly includes a manifold. The manifold contains a piezoelectric assembly. The volatile material dispenser further comprises a shroud and a refill that comprises a wick. The shroud defines a chimney that is centered along a longitudinal axis. The refill is removably coupled with the manifold. The refill is positioned entirely within the shroud when the refill is coupled with the manifold. The manifold includes an annular wall that extends from the manifold. A spring is disposed within the manifold and is coaxial with the annular wall. A top of the spring is wrapped around the annular wall and a bottom end of the spring is in contact with the piezoelectric assembly.

In some embodiments, the annular wall extends entirely around the longitudinal axis. In some embodiments, the base defines a sidewall, and the base includes at least one button that projects from the sidewall. In some embodiments, the button is configured to activate the piezoelectric assembly. In some embodiments, the volatile material dispenser further comprises a fan.

According to yet another aspect, a volatile material dispenser comprises a base that houses a printed circuit board. The base includes a port that is capable of being electronically coupled with a power source. The volatile material dispenser also comprises a stand assembly and a shroud. The stand assembly is coupled with the base. The stand assembly includes a platform, a stand that extends from the platform, and a manifold that extends from the stand. The manifold includes a refill chassis and a crown. The manifold contains a piezoelectric element. The shroud defines a chimney that is centered along a longitudinal axis. The crown includes an annular wall that extends from the crown. The annular wall is coaxial with the chimney. A spring is disposed within the manifold and is coaxial with the annular wall. A top end of the spring is wrapped around the annular wall and a bottom end of the spring applies a force against the piezoelectric element.

In some embodiments, the crown comprises a top surface. In some embodiments, a portion of the annular wall extends above the top surface of the crown and a portion of the annular wall extends below the top surface of the crown. In some embodiments, the annular wall extends entirely around the longitudinal axis. In some embodiments, the volatile material dispenser further comprises a refill that includes a wick, and the refill is removably coupled with the refill chassis. In some embodiments, the refill is positioned above the platform and entirely within the shroud when the refill is coupled with the refill chassis.

BRIEF DESCRIPTION OF THE DRAWINGS

FIG. 19 is a detail view of an upper portion of the internal stand of FIG. 14;

FIG. 20 is a detail view of the upper portion of the internal stand of FIG. 19 with the refill of FIG. 10 inserted into a manifold of the stand;

DETAILED DESCRIPTION

The present disclosure is directed to volatile material dispensers or diffusers and methods of emitting volatile materials therefrom. While the present disclosure may be embodied in many different forms, several specific embodiments are discussed herein with the understanding that the present disclosure is to be considered only an exemplification of the principles of the disclosure, and it is not intended to limit the disclosure to the embodiments illustrated. Throughout the disclosure, the terms "about" and "approximately" refer to a range of values ±5% of the numeric value that each term precedes.

The volatile material dispensers or diffusers disclosed herein are multisensory devices that use a piezoelectric engine to create and eject micro droplets of liquid fragrance into the surrounding environment. The volatile material dispensers are configured to accept a replaceable fragrance oil bottle or refill. The dispensers are further configured to run on low voltage, and feature a fragrance intensity selector that provides visual feedback to a user in the form of a glowing light. The dispenser includes a shroud, a stand assembly, and a base that collectively house control buttons, a power connector, lights, and a piezo engine. The shroud is primarily decorative and provides a light transmission shade. Before a first use of the volatile material dispenser, the shroud is removed to insert a fragrance oil bottle or refill into the stand assembly.

Still further, the volatile material dispensers disclosed herein include improvements to a piezo plate-to-wick interface, which, through testing, has been found to increase system performance and consistency. Specifically, testing has revealed a sensitivity and variations in consistency based upon a downward contact force of the piezo plate and a top of the wick. For example, a constant force provides a more consistent output and minimized variance. Through testing, it has also been determined that force differences can create variances in output rate as a result of changing load conditions on the piezo plate. Too high of a downward load onto the piezo plate has been found to dampen an amplitude of mechanical vibration of the piezo plate, which can minimize droplet output. Conversely, too light of a downward force has been found to limit the plate-to-wick interface contact, which has been found to result in high, undamped output. This is likely because under such circumstances, contact between the piezo plate and the wick can be lost entirely.

Figure 1:
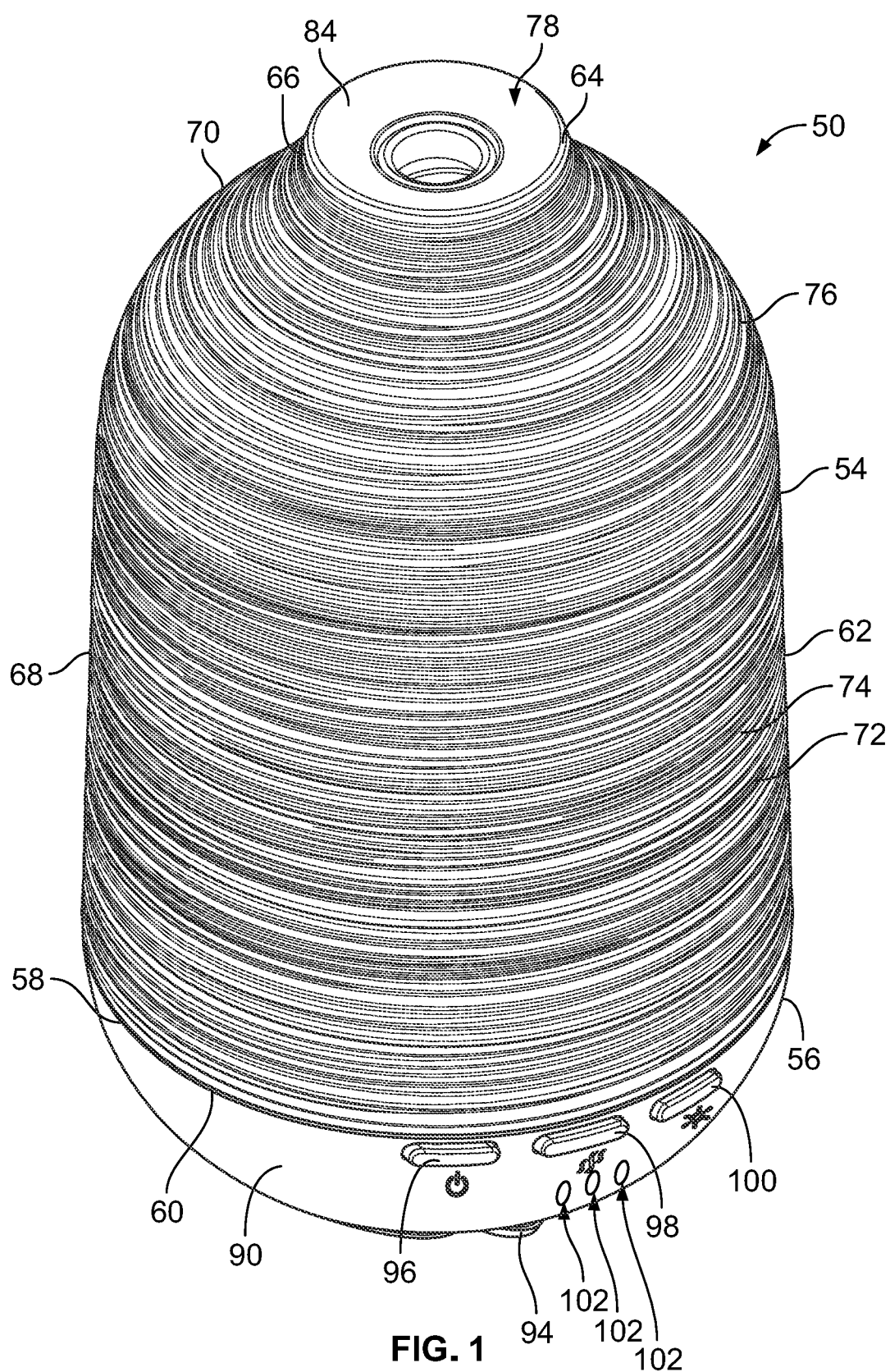
FIG. 1 is a front, top, and right isometric view of a volatile material dispenser in accordance with the present disclosure.
Figure 2:
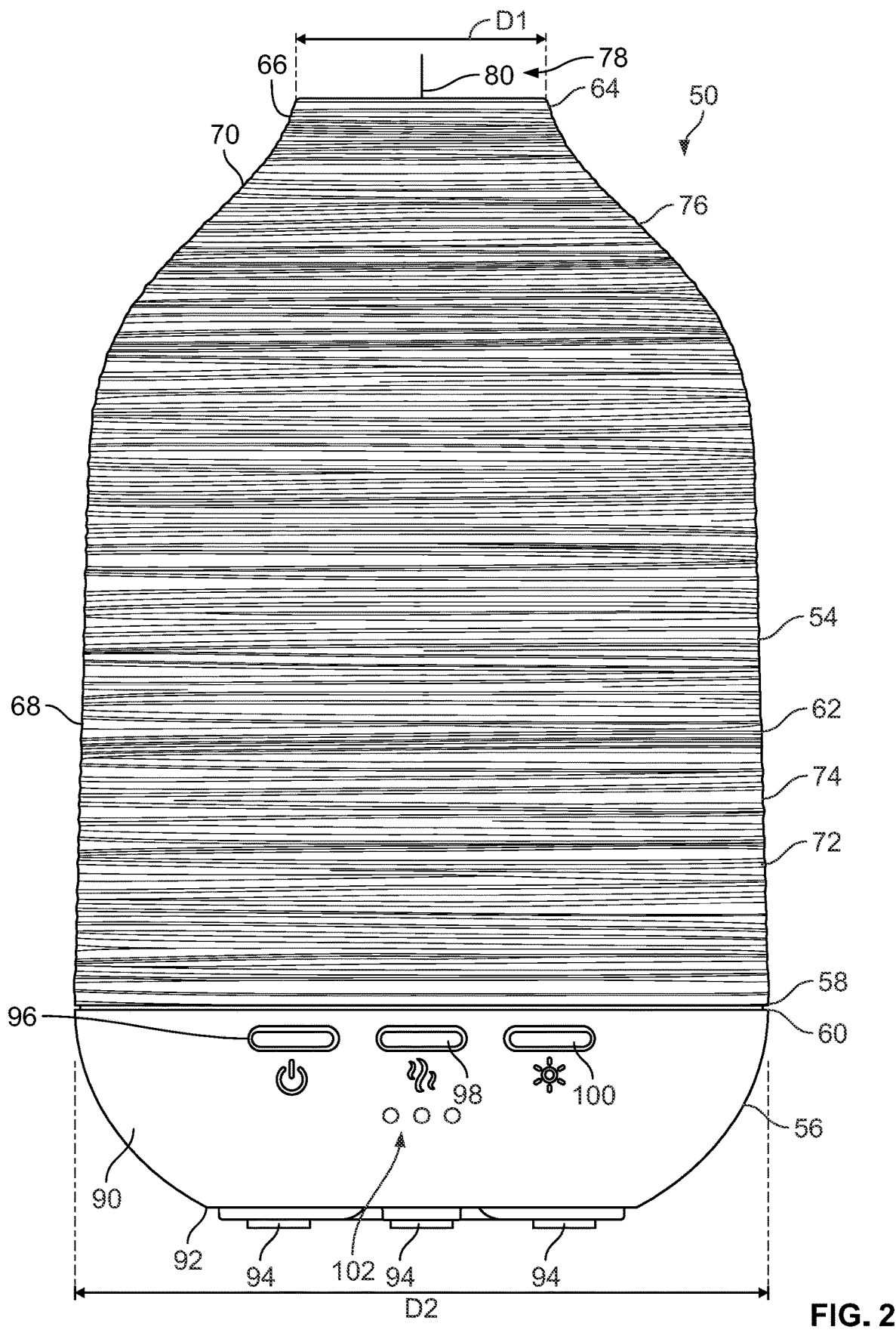
FIG. 2 is a front elevational view of the volatile material dispenser of FIG. 1.

Referring now to the drawings, FIGS. 1-7 depict a volatile material dispenser 50 embodying aspects of the present disclosure. The dispenser 50 may be adapted to accommodate a refill 52 (see FIGS. 10-12) and dispense a volatile material in the form of water and/or fragranced oil from the refill 52. Referring specifically to FIGS. 1 and 2, the dispenser 50 includes a shroud or cover 54 and a base 56. The shroud 54 defines a lower edge 58 that interfaces with an upper edge 60 of the base 56. A sidewall 62 of the shroud 54 extends upward from the lower edge 58 toward a lip 64 at an upper end 66 of the shroud 54. The sidewall 62 of the shroud 54 defines a frustoconical lower portion 68 and a spline-shaped upper portion 70, when viewed in cross-section. A plurality of ridges or design features 72 are provided along an outer surface 74 of the shroud 54. Any number of design features 72 may be provided along the outer surface 74 of the shroud 54. The lower portion 68 and the upper portion 70 of the shroud 54 intersect at a rounded shoulder 76, from which the upper portion 70 extends toward a chimney 78 that is centered about a central longitudinal axis 80 (FIG. 2) of the dispenser 50. The chimney 78 is defined as the portion interior to the lip 64. In some embodiments, the shroud 54, and the base 56 comprise polypropylene (PP), however, the shroud 54 and the base 56 may comprise a wide variety of polymeric materials.

Still referring to FIGS. 1 and 2, the sidewall 62 along the upper portion 70 extends from the shoulder 76 toward the lip 64. Referring to FIG. 1, a flange 84 of the shroud 54 extends downward from the lip 64 toward the longitudinal axis 80 and into the chimney 78. The angle at which the flange 84 extends downward from the lip 64 is best illustrated in the cross-sectional views of FIGS. 13 and 14. Referring specifically to FIG. 2, while the chimney 78 may define a variety of diameters, the chimney 78 is illustrated having a diameter D1 that is about 30% of a widest diameter D2 of the shroud 54 taken at the lower edge 58 thereof. In some embodiments, the diameter D1 may be between about 5% and about 60% of the diameter D2, or between about 10% and about 45% of the diameter D2, or between about 15% and about 35% of the diameter D2. In some embodiments, the diameter D1 is about 10%, or about 20%, or about 30%, or about 40%, or about 50% of the diameter D2.

Referring again to FIGS. 1 and 2, the base 56 also defines a sidewall 90 that extends from the upper edge 60 of the base 56 downward, toward a bottom wall 92 thereof. A plurality of feet 94 extend downward from the bottom wall 92, and are provided to allow the dispenser 50 to rest upon a flat surface (not shown). The sidewall 90 of the base 56 is generally curved, and extends from the upper edge 60 downward and inward, toward the longitudinal axis 80. The sidewall 90 of the base 56 may define a radius of curvature along a portion of the sidewall 90. Still further, a first button 96, a second button 98, and a third button 100 extend from the base 56 outward, away from the longitudinal axis 80. The first button 96, the second button 98, and the third button 100 may be used for a variety of purposes, and may have a variety of different functions, as discussed hereinafter below.

Referring to FIG. 2, the first button 96, the second button 98, and the third button 100 may be provided along the base 56 of the dispenser 50. The first button 96 may be a power button that allows a user to turn the dispenser 50 on and off. The second button 98 may be a fragrance strength adjusting button that allows a user to cycle through settings of the dispenser 50. For example, the user may be able to switch between a low setting, a medium setting, and a high setting. A plurality of light indicators 102 may be visible through the base 56 adjacent or below the second button 98. The light indicators 102 may provide visual feedback to a user regarding the strength or intensity of the chosen setting. In the illustrated embodiment, there are three of the light indicators 102. When the low setting is selected, one of the light indicators 102 may be illuminated; when the medium setting is selected, two of the light indicators 102 may be illuminated; and when the high setting is selected, three of the light indicators 102 may be illuminated. The third button 100 may be a light illumination button that, when pressed by a user, cycles through various light brightness settings and color settings.

A user can select an option for light and/or color based on personal preference. Further, in some embodiments, after being turned on via the first button 96, the dispenser 50 may run for a pre-determined amount of time, e.g., 8 hours, and may subsequently enter into a sleep mode for a pre-determined amount of time, e.g., 16 hours. The dispenser 50 may repeat this cycle every 24 hours unless manually turned off via the first button 96 by a user. In some embodiments, the dispenser 50 includes an automatic shut-off function that deactivates the dispenser 50 after a particular period of time, for example, after seven 24-hour cycles, i.e., one week. In some embodiments, a limit switch (not shown) may be provided along the base 56 which only allows the dispenser 50 to be activated when the shroud 54 is engaged with the base 56.

Figure 3:
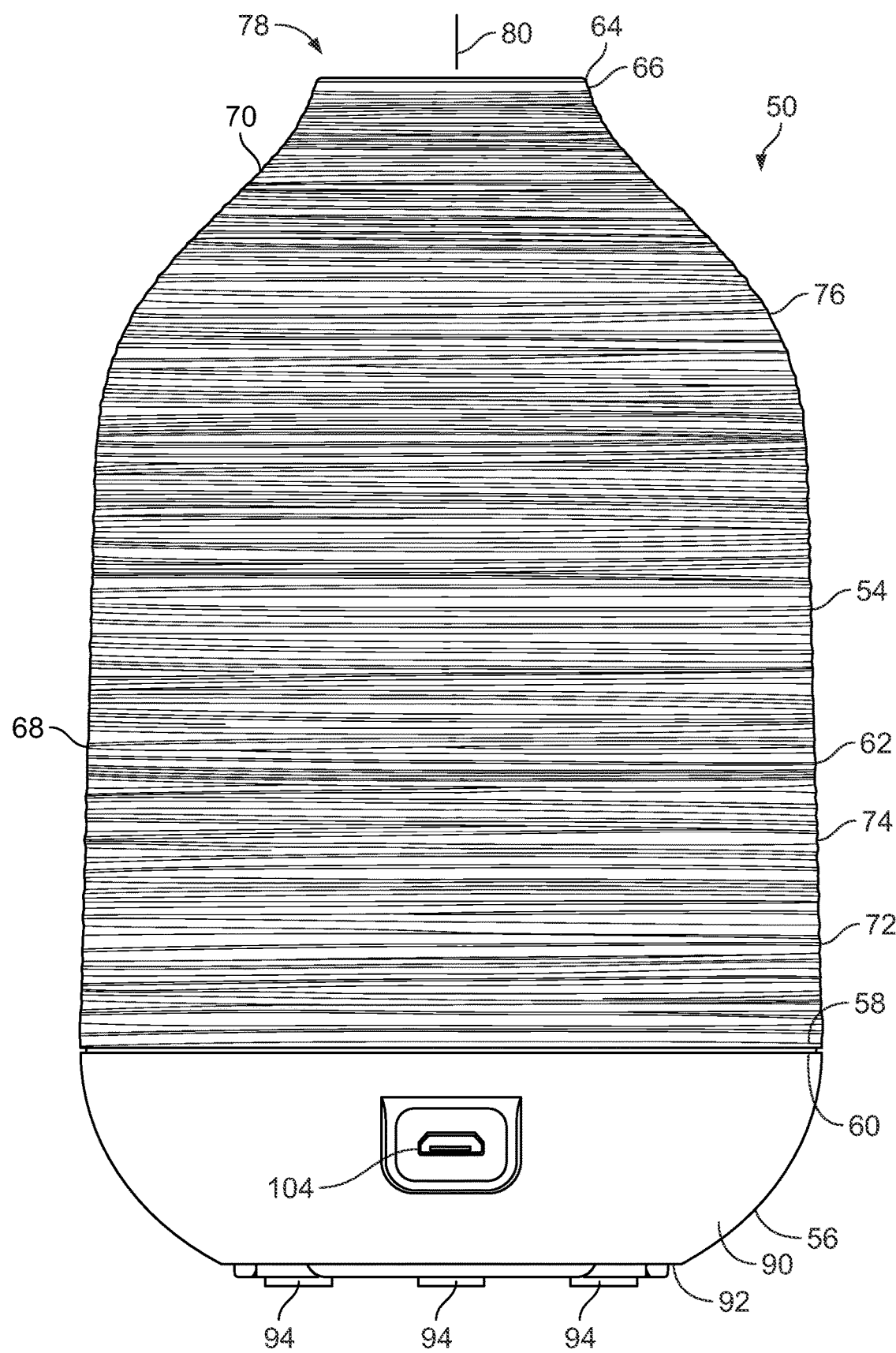
FIG. 3 is a rear elevational view of the volatile material dispenser of FIG. 1.
Figure 4:
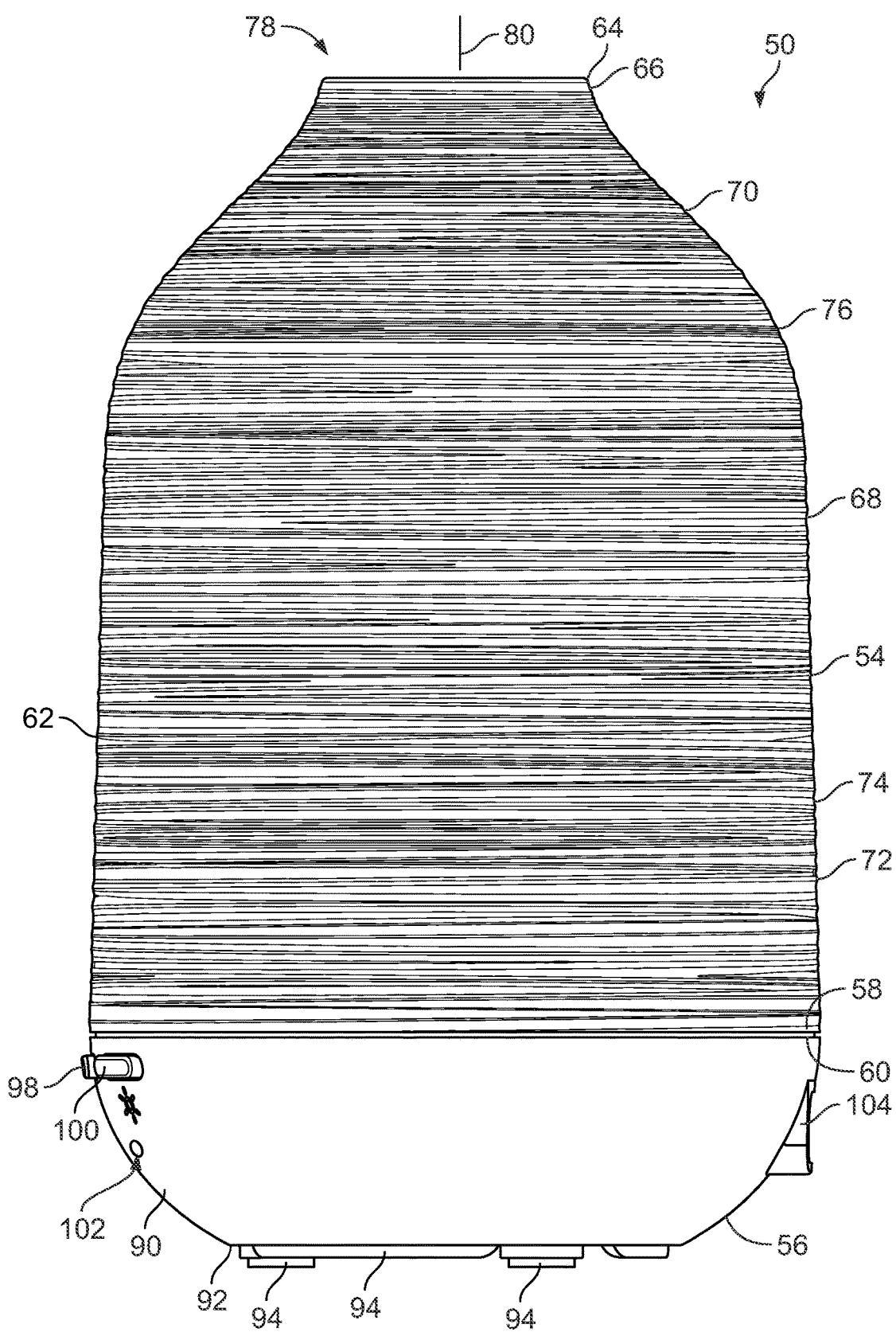
FIG. 4 is a left side elevational view of the volatile material dispenser of FIG. 1.

Referring now to FIG. 3, a rear view of the dispenser 50 is shown. As illustrated in the rear view, the dispenser 50 further includes a low voltage receptacle or port 104 for receiving a low-voltage electrical connector of a low voltage wire, such as a USB cord (not shown). In some embodiments, electrical prongs, a cord, or another suitable electrical connector may be electrically coupled with the dispenser 50 so as to allow electrical power to be provided to the dispenser 50. FIG. 4 illustrates a left side of the dispenser 50. The buttons 96, 98, 100 and the port 104 extend outward from the sidewall 90 of the base 56 and cause interruptions of the sidewall 90. As a result, the sidewall 90 of the base is rotationally symmetrical, but the entire base 56 is symmetric about a plane 13-13 (see FIG. 5) that bisects the second button 98 and the port 104. Additional features may be provided within or along the shroud 54 and/or the base 56. Further, additional bodies defining one or more sidewalls (not shown) may be provided between, above, or below the base 56 and the shroud 54.

Figure 5:
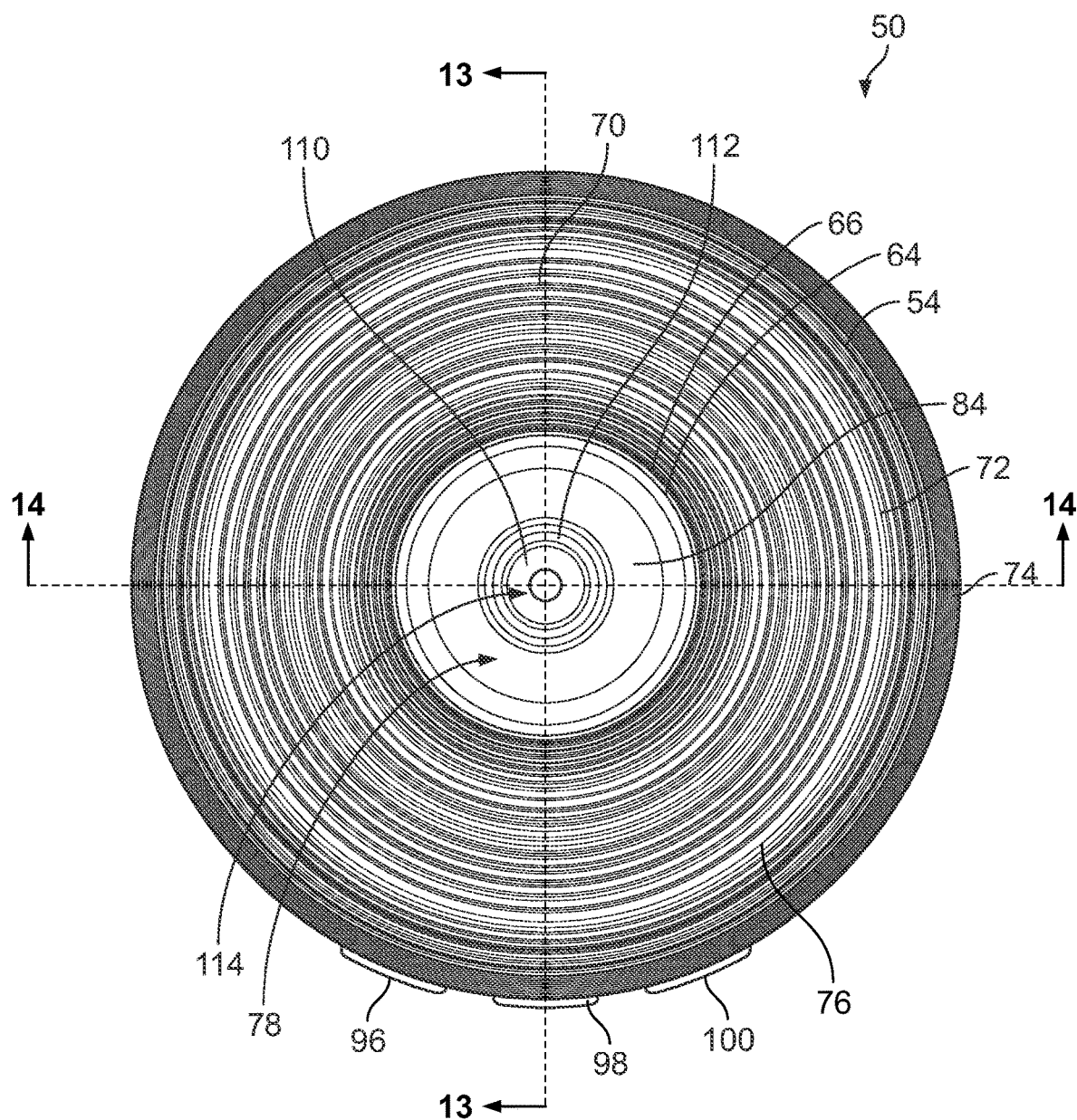
FIG. 5 is a top plan view of the volatile material dispenser of FIG. 1.

Referring now to FIG. 5, a top view of the dispenser 50 is depicted. The chimney 78 is shown in greater detail, which is centered along the longitudinal axis 80. A piezoelectric assembly 110 is shown within the chimney 78, which is also centered along the longitudinal axis 80. An annular piezoelectric element 112 is also visible through the chimney 78, the piezoelectric element 112 defining a circular rim of the piezoelectric assembly 110. The piezoelectric element 112 includes a central aperture 114 through which liquid volatile within the refill is dispersed when the dispenser 50 is activated. When the dispenser 50 is activated, a stream of the volatile is dispensed through the chimney 78 of the shroud 54 and out of the dispenser 50, as discussed in greater detail hereinafter below.

Figure 6:
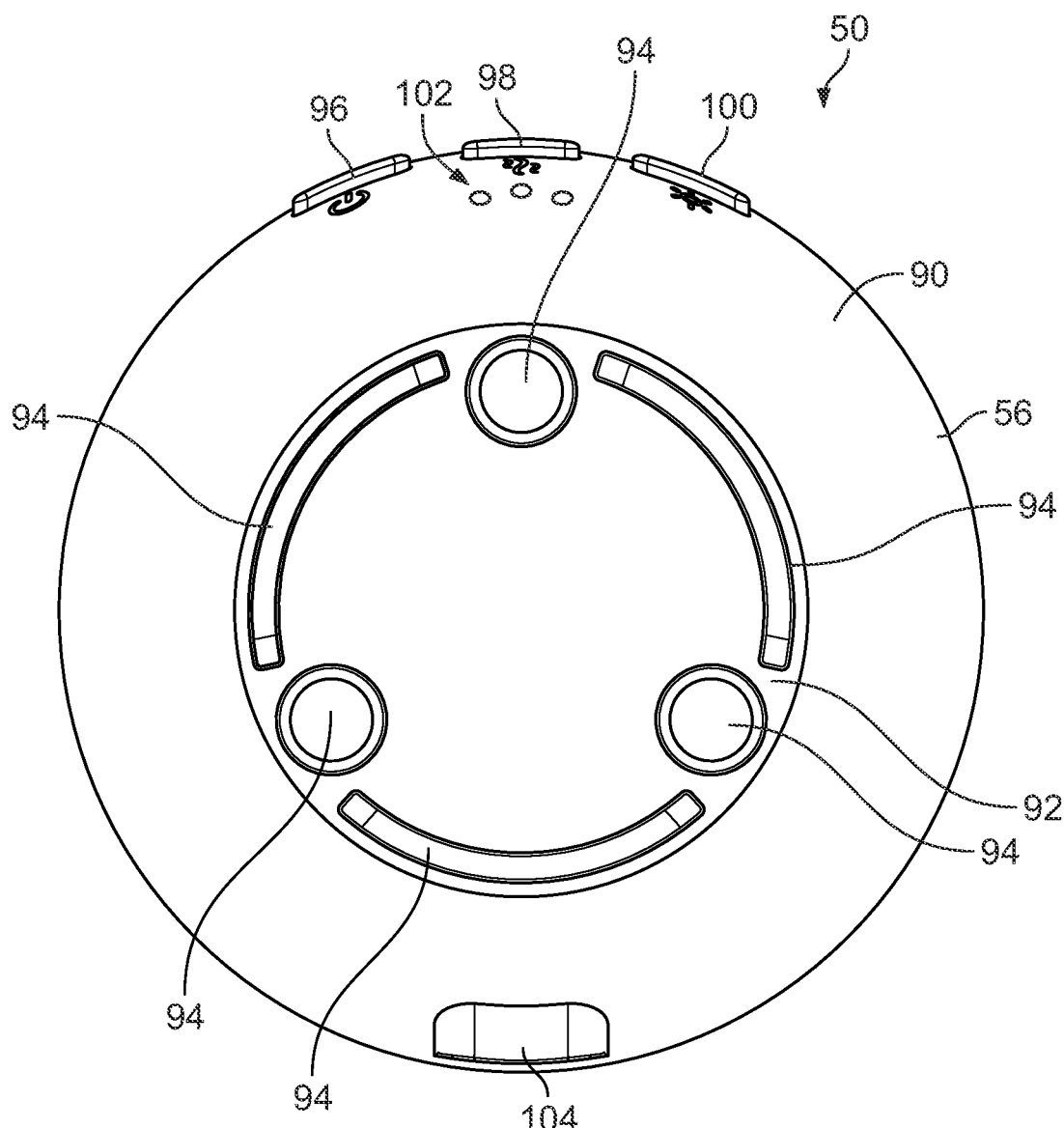
FIG. 6 is a bottom plan view of the volatile material dispenser of FIG. 1.

Referring now to FIG. 6, the bottom wall 92 of the base 56 is shown in greater detail. The plurality of feet 94 extend from the bottom wall 92. The plurality of feet 94 are provided in a generally circular shape, with alternating circular and elongate feet 94. Alternative configurations or shapes of the feet 94 are contemplated, while in some embodiments additional structure may be included in addition to the feet 94. Still further, in some embodiments, there are no feet 94 or other types of stability mechanisms that retain the dispenser 50 in an upright configuration. As further illustrated in FIG. 6, the second button 98 and the port 104 are provided 180 degrees offset from one another about the longitudinal axis 80. The first button 96, the second button 98, and the third button 100 are also equally spaced apart from one another. Alternative configurations of the port 104 and the buttons 96, 98, 100 are also contemplated.

Figure 7:
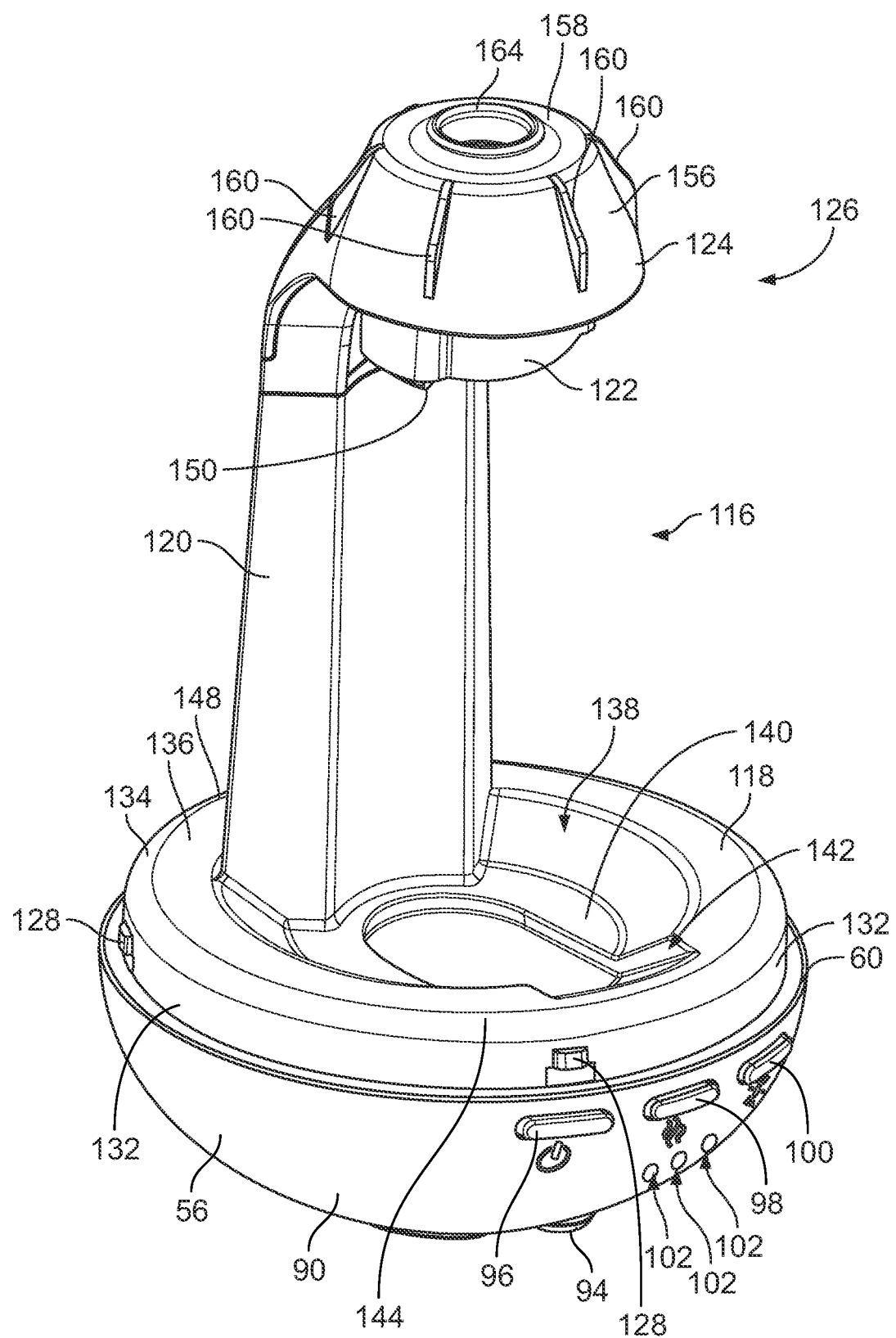
FIG. 7 is a front, top, and right isometric view of an internal stand and a base of the volatile material dispenser of FIG. 1 with a shroud having been removed for clarity.
Figure 8:
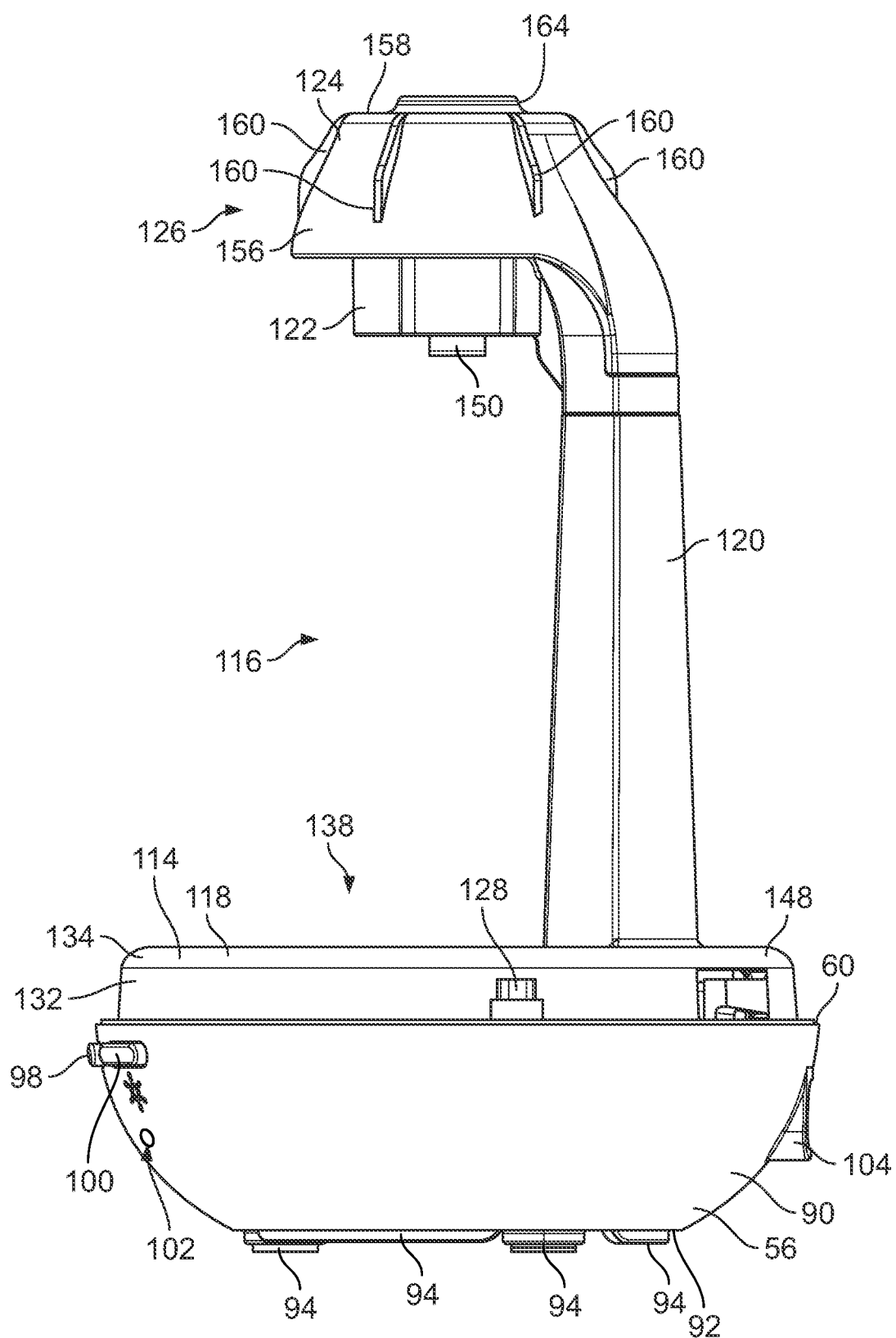
FIG. 8 is a right side elevational view of the stand and base of FIG. 7.
Figure 9:
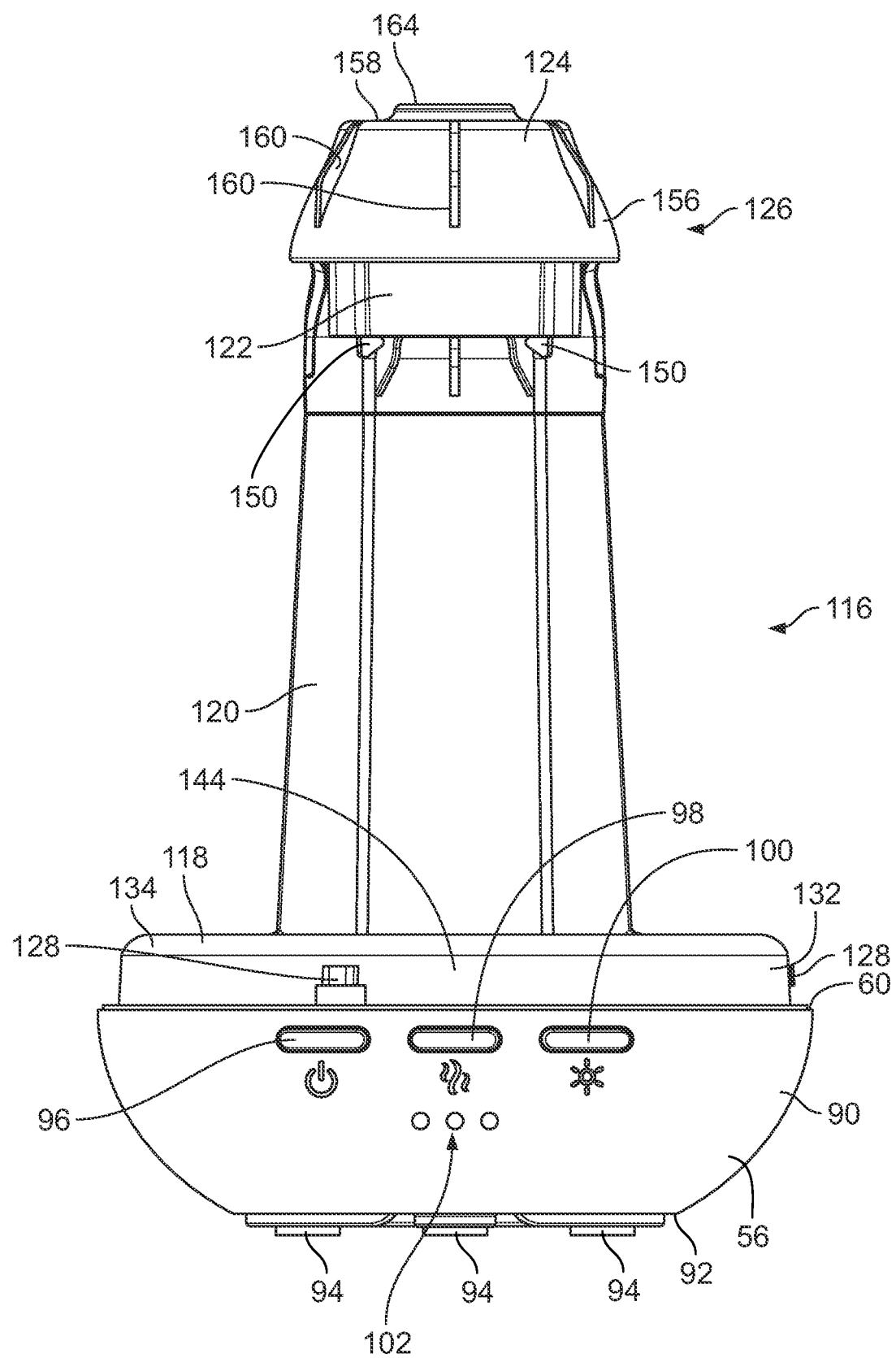
FIG. 9 is a front elevational view of the stand and base of FIG. 7.

Referring now to FIGS. 7-9, a stand assembly 116 of the dispenser 50 is shown, with the shroud 54 having been removed for clarity. The stand assembly 116 includes a platform 118, a stand 120, a refill chassis 122, and a crown 124. The refill chassis 122 and the crown 124 define a manifold 126 that retains the refill 52 and the piezoelectric assembly 110. The platform 118 extends upward from the base 56 and is inset from the sidewall 90 thereof. A plurality of retention protrusions 128 extend outward from the platform 118, which operate to engage the shroud 54 when it is coupled with the base 56. The retention protrusions 128 are a form of retention mechanism that couples the shroud 54 with the base 56. Alternative retention mechanisms may include elements that cause a snap fit, a friction fit, or an interference fit. The platform 118 is permanently coupled with the base 56 via a plurality of fasteners 130 (see FIG. 13), the channels for which are covered by the feet 94 after assembly thereof. The fasteners 130 are a form of fastening mechanism, additional examples of which include rivets, nails, bolts, or cables.

The platform 118 defines an outer cylindrical surface 132 that extends upward to a corner 134. An angled surface 136 extends inward and downward from the corner 134, toward a well 138 defined within a central portion 140 of the platform 118. A slot 142 is defined within the angled surface 136 along a front portion 144 of the platform 118. The slot 142 may be included to aid in the insertion of the refill 52 into an operable configuration. The well 138 may include additional features that aid in retaining the refill 52 or another component. For example, the well 138 of the platform 118 may be sized and shaped to retain a cap 146 (see FIG. 10) of the refill 52 after the cap 146 has been removed from the refill 52.

Still referring to FIGS. 7-9, the stand assembly 116 includes the stand 120, which extends upward from the platform 118 along a rear portion 148 thereof. The stand assembly 116 comprises a unitary piece that extends upward from the platform 118 toward the manifold 126, which extends inward, and aligns with the longitudinal axis 80. Elements of the stand assembly 116 may also comprise polypropylene or another type of polymeric material. As noted above, the manifold 126 includes the crown 124 and the refill or chassis 122, which extends downward from the crown 124. The chassis 122 includes the first and second tabs 150 that depend downward to retain an annular rim 152 (see FIG. 11) of the refill 52. As will be discussed in greater detail hereinafter below, the first and second tabs 150 may be formed to flex outward when the refill 52 is laterally inserted into the chassis 122 until the rim 152 of the refill engages with the tabs 150.

The refill 52 may be removed from the tabs 150 by a user grabbing the refill 52 and laterally pulling the refill down. In some embodiments, the forces required for insertion and removal of the refill 52 are low enough to simply allow for lateral insertion and removal. However, in some embodiments, the refill 52 may be removed by squeezing the tabs 150 to deflect the tabs 150 outward, thereby releasing the rim 152 from engagement therewith. In some embodiments, the refill 52 may be disengaged by rotating the refill 52 such that threading 154 (see FIG. 11) allows the refill to be rotated and translate downward, away from the crown 124, for removal from the manifold 126. Alternative removal mechanisms may be implemented, such as one or more buttons (not shown) that could be depressed to cause the refill 52 to be released from the chassis 122.

With continued reference to FIGS. 7-9, the crown 124 extends upward from the chassis 122 and defines a generally frusto-conical side surface 156 that terminates at a top surface 158. A plurality of ribs 160 are radially disposed along the side surface 156, which may be formed to aid in physical engagement with an underside 162 (see FIG. 13) of the shroud 54. The ribs 160 are spaced apart about the longitudinal axis 80. An annular wall or a cylindrical wall 164 extends upward from the top surface 158 of the crown 124, the cylindrical wall 164 having a center that is coaxial with the longitudinal axis 80. The cylindrical wall 164 is also coaxial with the chimney 78 defined by the shroud 54. The cylindrical wall 164 is aligned with the second button 98 and the port 104, i.e., the plane 13-13 (see FIG. 5) extends through all of the cylindrical wall 164, the second button 98, and the port 104. While the shroud 54 generally comprises radial symmetry notwithstanding the design features 72, the platform 118, the stand 120, and the manifold 126 may be characterized as being symmetric about the plane 13-13 that intersects the second button 98 and extends through the longitudinal axis 80.

Figure 10:
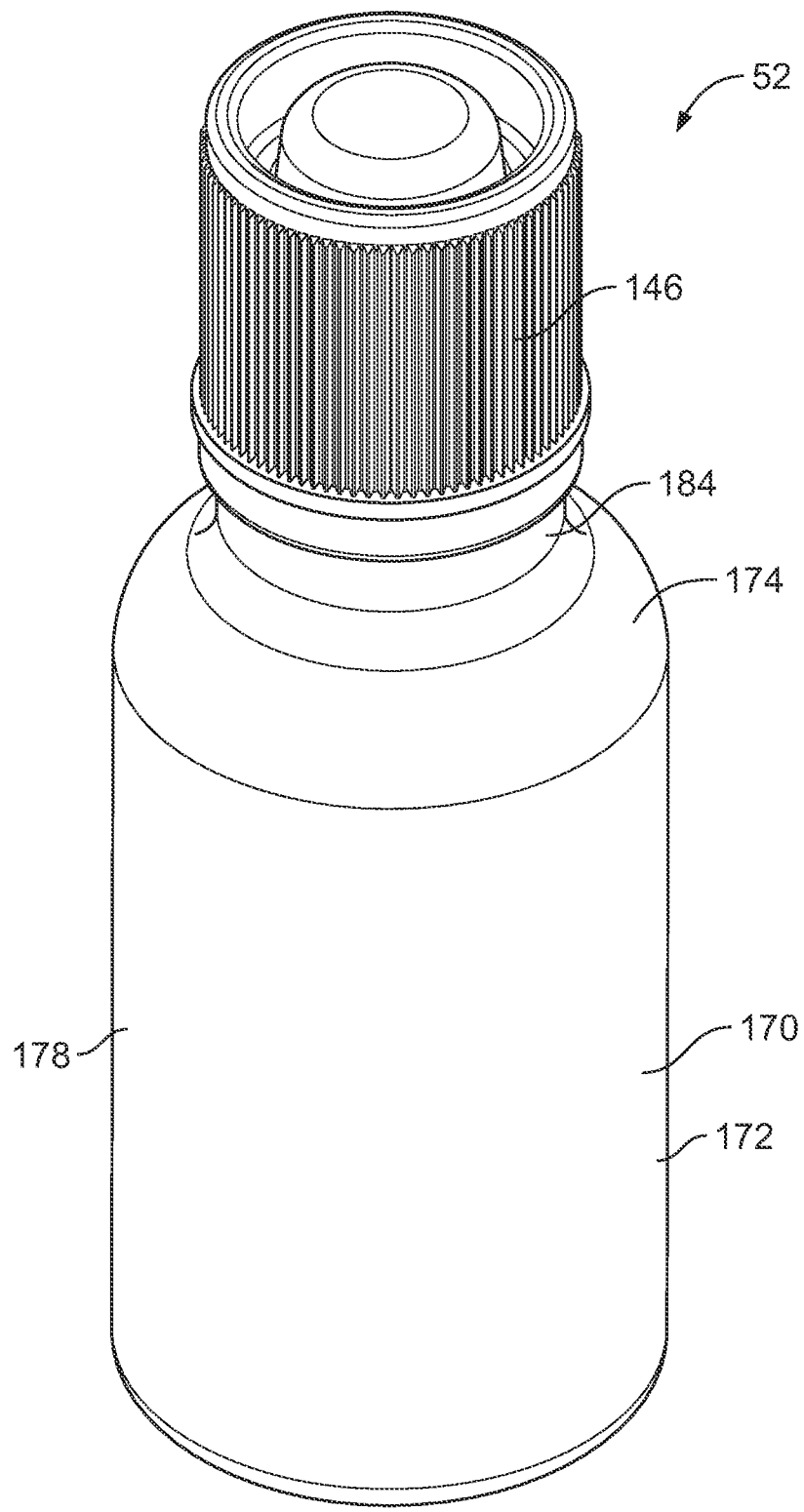
FIG. 10 is a front, top, and right isometric view of a refill for use with the volatile material dispenser of FIG. 1.
Figure 11:
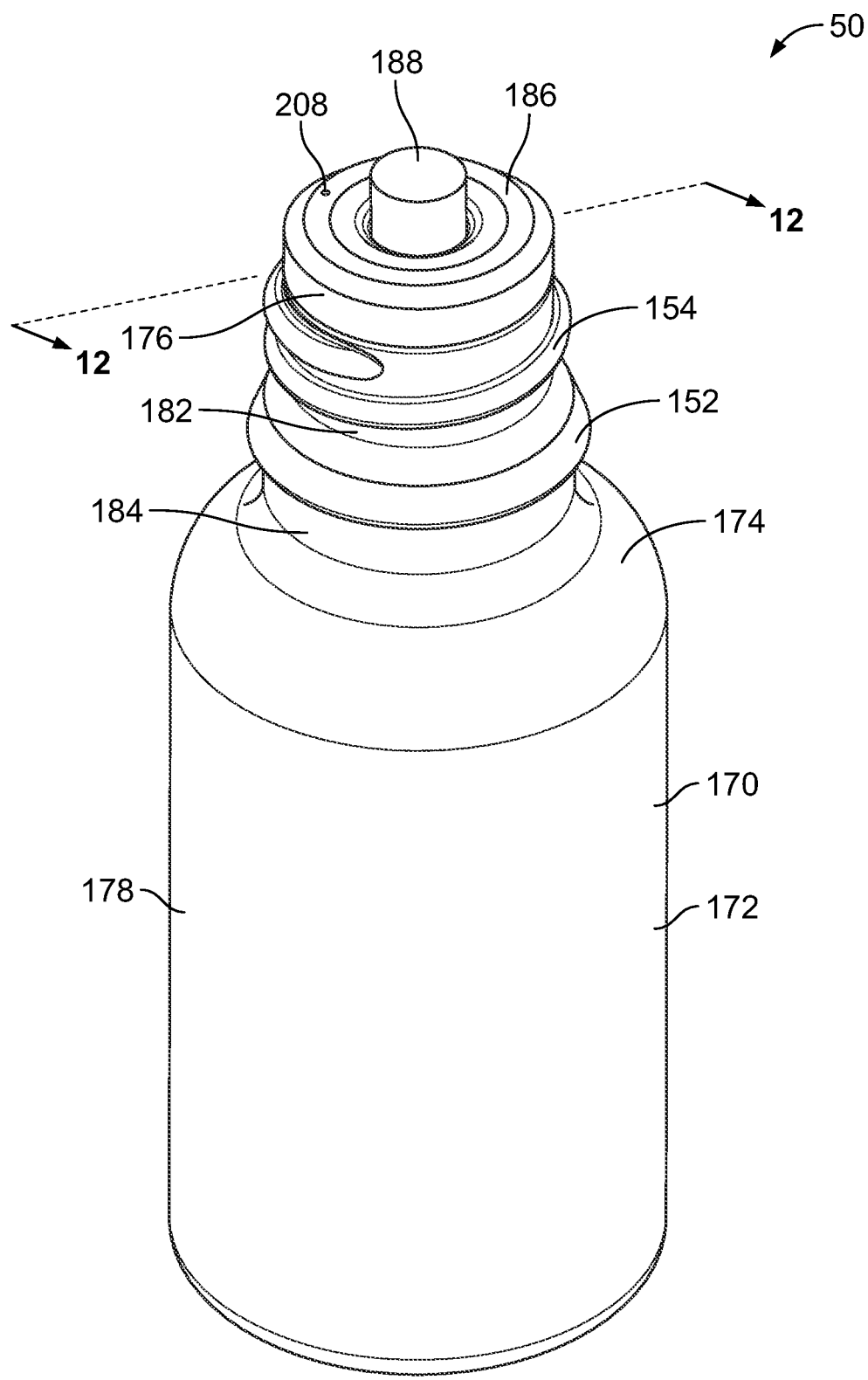
FIG. 11 is a front, top, and right isometric view of the refill of FIG. 10 with a cap having been removed.
Figure 12:
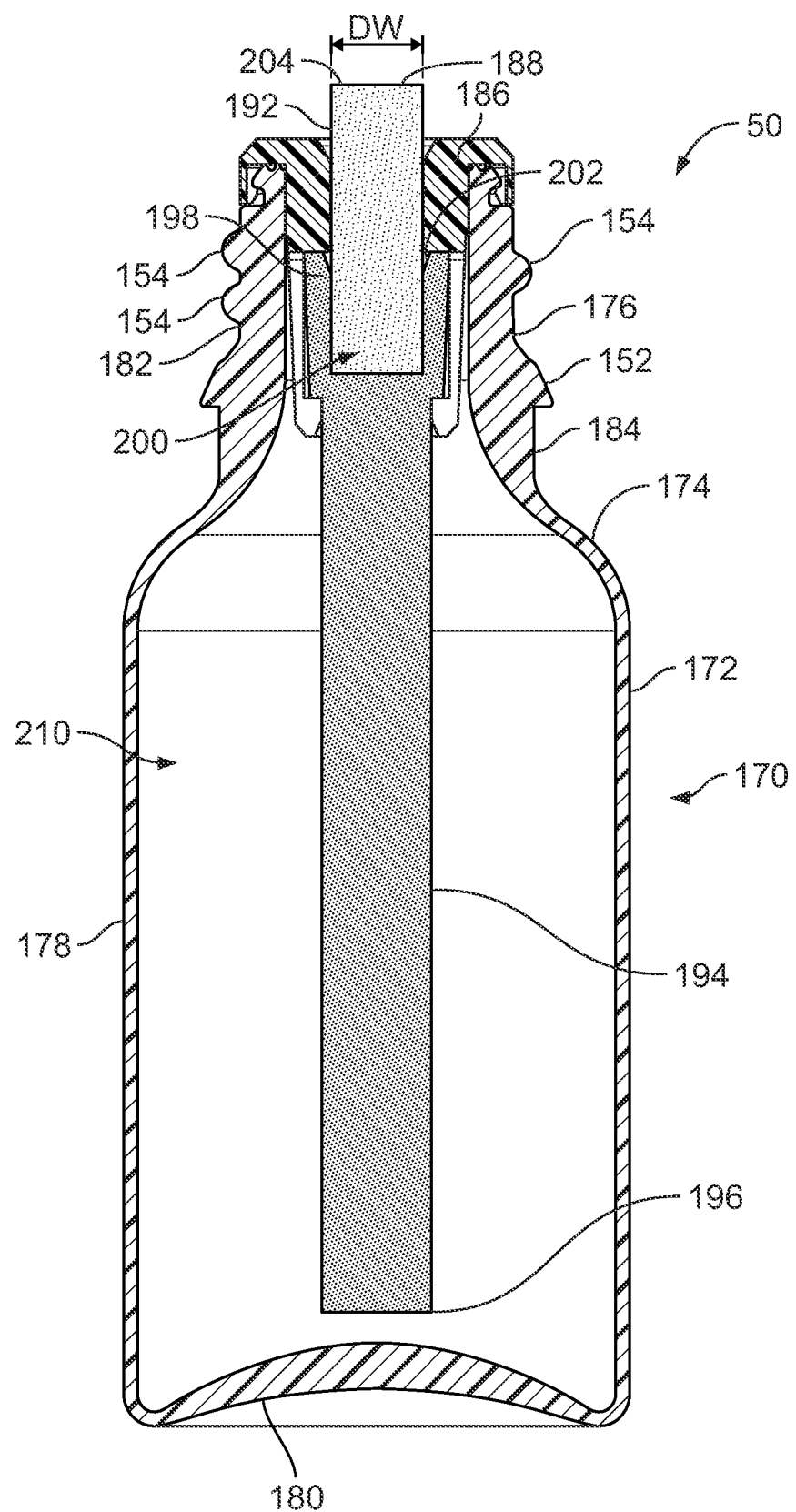
FIG. 12 is a side cross-sectional view of the refill taken through line 12-12 of FIG. 11.

Referring now to FIGS. 10-12, the refill 52 is shown in greater detail. The refill 52 comprises a cap 146 and a container 170 defining a body 172, a shoulder 174, and a head 176. The body 172 comprises a cylindrical outer wall 178 that extends upward from a lower wall 180 thereof to the shoulder 174. The head 176 extends upward from the shoulder 174 and defines a finish 182. The head 176 joins the body 172 at the shoulder 174. The refill 52 further includes a cap 146 that is threadably coupled with the threading 154 (see FIGS. 11 and 12) disposed along a neck 184 of the refill 52. Referring to FIG. 12, the container 170 holds a volatile material therein, and the container 170 is adapted to be retained within the dispenser 50. A wick holder or plug 186 is disposed within the neck 184 for holding a wick 188 with a first end of the wick 188 in contact with the volatile material and a second end of the wick 188 extending out of the container 170 through the neck 184. In illustrative embodiments, the wick 188 may be formed of extruded fibers that are bundled together into the shape of a rod.

Still referring to FIG. 12, the wick 188 may be formed of rope or one or more cotton cords. The wick 188 comprises an upper wick 192 and a lower wick 194. The upper wick 192 has different properties than the lower wick 194, however, in some embodiments, the upper wick 192 and the lower wick 188 have the same properties. In a preferred embodiment, the upper wick 192 is pliable and/or fibrous, while the lower wick 194 may be sintered or more rigid than the upper wick 192. The upper wick 192 may have properties that allow the upper wick 192 to deform into the piezoelectric assembly 110. The lower wick 194 includes a lower end 196 disposed adjacent and spaced apart from the lower wall 180, and has an upper end 198 that is engaged with the upper wick 192. The upper wick 192 is nested within a wick cavity 200 at the upper end 198 of the lower wick 194. An upper cambered or angled surface 202 surrounds an inner periphery of the wick cavity 200. The upper angled surface 202 may aid in alignment of the upper wick 192 within the wick cavity 200 during assembly of the refill 52. The upper wick 192 is snugly retained by the plug 186 and has a distal end 204 that extends upward, out of the container 170. The wick 188 may be formed in any suitable shape or of any suitable material, however, the upper wick 192 is preferably more pliable than the lower wick 194. The plug 186 is retained within the neck 184 of the refill 52 by an interference fit, a friction fit, or in any other suitable manner that holds the plug 186 in place within the neck 184.

Still referring to FIG. 12, the shoulder 174 of the container 170 extends upward to the finish 182 and the neck 184 of the head 176. The threading 154 circumscribes the neck 184 and extends outward therefrom. The annular rim 152 also circumscribes the finish 182, which may be used to engage the refill 52 with the depending tabs 150 of the chassis 122. The lower wall 180 of the refill 52 is generally concave and extends upward, toward the wick 188. An air hole 208 (see FIG. 11) is provided within the plug 186 to allow air to enter into a cavity 210 of the refill 52 as liquid (not shown) is dispersed out of the refill 52 into the surrounding atmosphere. Although a refill 52 is shown and described with particularity, it is contemplated that any type of refill may be used with variations of the dispensers described herein. For example, a refill with a flexible container may be utilized. Still further, the delivery system (i.e., the wick) may be different and/or the size and/or the shape of the container 170 may be different than those described herein.

The volatile material disposed in the container 170 may be any type of volatile material adapted to be dispensed into an environment. For example, the material within the container 170 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances and/or preservatives. In fact, any fluid may be provided within the container 170.

Figure 13:
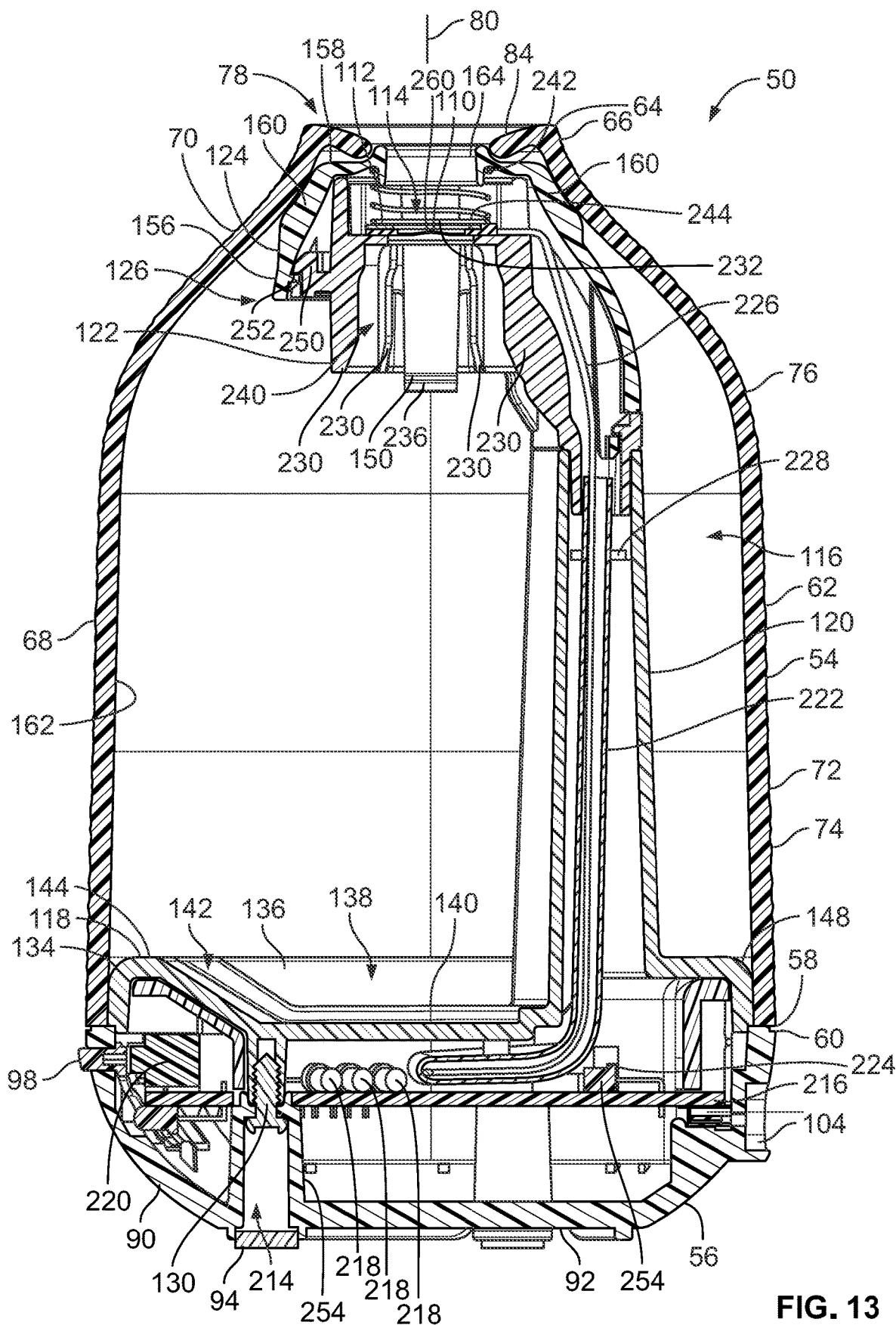
FIG. 13 is a cross-sectional view of the volatile material dispenser taken through line 13-13 of FIG. 5.
Figure 14:
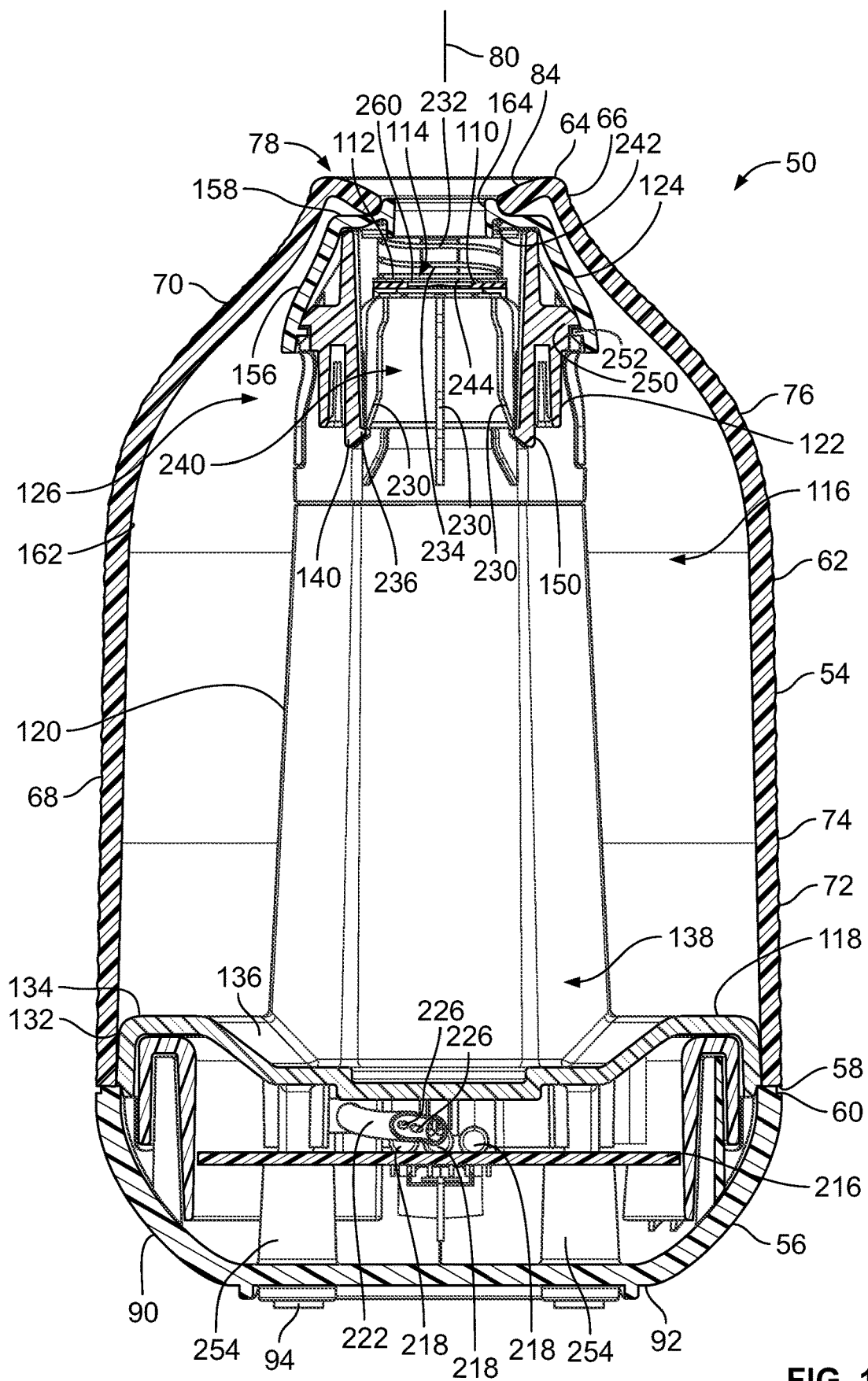
FIG. 14 is a cross-sectional view of the volatile material dispenser taken through line 14-14 of FIG. 5.

Referring now to the cross-sectional views of FIGS. 13 and 14, internal components of the dispenser 50 are shown in greater detail. Referring to FIG. 13, the base 56 is shown being connected with the stand assembly 116 via one of the fasteners 130. The fastener 130 is disposed within a fastener channel 214 that is covered from view by one of the feet 94 after the stand assembly 116 has been fastened to the base 56. In the present embodiment, there are three fasteners 130 that secure the base 56 with the stand assembly 116, however, only a single fastener 130 is shown in the cross-section of FIG. 13.

A printed circuit board (PCB) 216 is shown intermediate the base 56 and the stand assembly 116. A plurality of light emitting diodes (LEDs) 218 are shown electrically coupled with the PCB 216, the plurality of LEDs 218 being disposed above the PCB 216. In some embodiments, the plurality of LEDs 218 are disposed above and below the PCB 216. In some embodiments, some of the LEDs 218 are disposed adjacent the front, rear, and sides of the dispenser 50. As noted above, the LEDs 218 are intended to be used to emit light through the shroud 54 depending on the chosen setting, which can vary based on user preference. The LEDs 218 may alternatively be positioned in any suitable location within the dispenser 50. The one or more LEDs 218 may indicate that the dispenser 50 is on or off, may provide an alert, and/or may provide any other suitable indicator for a user. As noted above, a color and/or a brightness of the LEDs 218 may be adjusted depending on a desired brightness and/or color of light to be emitted through the shroud 54.

For example, a first one of the LEDs 218 may illuminate a first color when the dispenser 50 is in a "Low" setting, a second one of the LEDs 218 may illuminate a second color when the dispenser 50 is in a "Medium" setting, and a third one of the LEDs 218 may illuminate a third color when the dispenser 50 is in a "High" setting. The third LED 218 may illuminate by itself in the high setting, or the lighting may be additive, such that both that first LED 218, the second LED 218, and the third LED 218 illuminate in the high setting, in which they may have the same or different colors and/or intensities. Alternatively, the first LED 218 may be illuminated when the dispenser 50 is plugged in but not on, and the second LED 218 may be illuminated when the dispenser 50 is plugged in and turned on. The dispenser 50 may include one or more separate openings in the shroud 54 or translucent portions of the shroud 54 to permit passage of the light emitted by each LED 218.

Still referring to FIG. 13, the second button 98 is shown protruding through the base 56. While the second button 98 is shown and referred to hereinafter below, the first button 96 and the third button 100 have an identical setup and functionality. The second button 98 is shown adjacent a switch 220, the switch 220 being operable to be adjusted between various settings of the dispenser 50. The switch 220 may be a push button switch that, when depressed, may cause the dispenser 50 to initiate one or more functions, such as turning the dispenser 50 on or off, causing an adjustment in the amount of fragrance that is dispensed, or adjusting the color or brightness of one or more of the LEDs 218. The switch 220 that is visible in FIG. 13 is one of a plurality of switches 220 that are visible in FIG. 16. The switches 220 may be the same switches, or the switches 220 may be different.

While the dispenser 50 is disclosed as having particular switches, one skilled in the art will appreciate the dispenser may include any number of switches and/or may include any suitable types of switches, for example, timing switches, on/off switches, setting switches, switches controlling another component within the assembly, such as a heater or a fan, and/or any other suitable switches.

Still referring to FIG. 13, the stand assembly 116 is shown in cross section, and the components that are disposed therein are visible. A wire tube 222 is shown, which extends from a terminal 224 that is disposed along the PCB 216, through the stand 120, and into the chassis 122. First and second wires 226 are disposed within the wire tube 222, which are electrically connected to the terminal 224 and to the piezoelectric assembly 110, which is disposed within the crown 124 of the stand assembly 116. The stand 120 is fixedly coupled with the chassis 122, which is also fixedly coupled with the crown 124. The stand 120, the chassis 122, and the crown 124 are all separate components, and may be coupled with one another via a snap fit, friction fit, interference fit, adhesive, or another method of coupling. As noted above, the stand 120, the chassis 122, and the crown 124 may all comprise polypropylene, or another polymeric material. The wires 226 are electrically coupled with the piezoelectric assembly 110, which is disposed within the crown 124. A wire tube guide 228 is further disposed within the stand 120, which is situated to retain the wire tube 222 within the stand 120. The wire tube guide 228 may comprise a horizontal portion having a cutout that retains the wire tube 222 in a static configuration. As further shown in FIG. 13, the piezoelectric assembly 110 is centrally located along the longitudinal axis 80. While the stand 120, the chassis 122, the platform 118, the base 56, and the shroud 54 are illustrated as comprising a polymer, other types of materials are contemplated.

Still referring to FIG. 13, a plurality of refill retaining ribs 230 are disposed along an interior of the chassis 122, which may be used to guide the neck 184 of the refill 52 upward, into position within the chassis 122 until the tabs 150 lock into place with the rim 152 along the refill 52. A spring 232 is shown, which is used to apply a force against the piezoelectric assembly 110. The spring 232 applies a constant force against the piezoelectric assembly 110 to retain it in a static configuration until the refill 52 as it is positioned within the chassis 122 by a user. When a user inserts the refill 52 into the dispenser 50, the piezoelectric assembly 110 is translated upward, causing the spring 232 to compress. The spring 232 defines a spring wire 234 that has a wire diameter, which is further discussed below. One of the tabs 150 is also shown, the tab 150 including an inwardly-depending catch 236 that is configured to translate outward, away from the longitudinal axis 80 as the refill 52 is being inserted into the chassis 122, and snaps back inward to secure the refill 52 in place within the chassis 122 by engaging with the rim 152 (see FIG. 20). The piezoelectric assembly 110 is disposed above a refill cavity 240, and is configured to receive the distal end 204 of the wick 188 when the refill 52 is inserted into the chassis 122.

Referring now to FIG. 14, another cross-sectional view of the dispenser 50 is shown. The wire guide 228 and the wires 226 are shown in cross-section, and a plurality of LEDs 218 are shown being disposed above the PCB 216. Further, additional refill guide ribs 230 are shown, which partially define a profile of the head 176 of the refill 52, and are configured to snugly receive the refill 52 within the chassis 122. The spring 232 comprises a top end 242 and a bottom end 244. The piezoelectric assembly 110 is also shown in FIG. 14, and is disposed below the bottom end 244 of the spring 232. The bottom end of the spring 232 may be fixedly attached with the piezoelectric assembly 110, or may be separate but disposed in physical contact with one another.

The bottom end 244 of the spring 232 is formed to receive the piezoelectric assembly 110, which is in turn formed to receive the upper wick 194 when the refill 52 is engaged therewith. The top end 242 of the spring 232 is wrapped around and secured to the cylindrical wall 164 of the crown 124. The chassis 122 includes an outer ledge 250 that is engaged with an inner ledge 252 of the crown 124. The chassis 122 and the crown 124 are snap fit together, however, the chassis 122 and the crown 124 may be coupled together in another fashion, such as via adhesive, fasteners, an interference fit, or a friction fit. Fastener walls 254 defining two of the fastener channels 214 are also shown clearly in FIG. 14, the fastener walls 254 extending between the bottom wall 92 of the base 56 and the platform 118.

Figure 15:
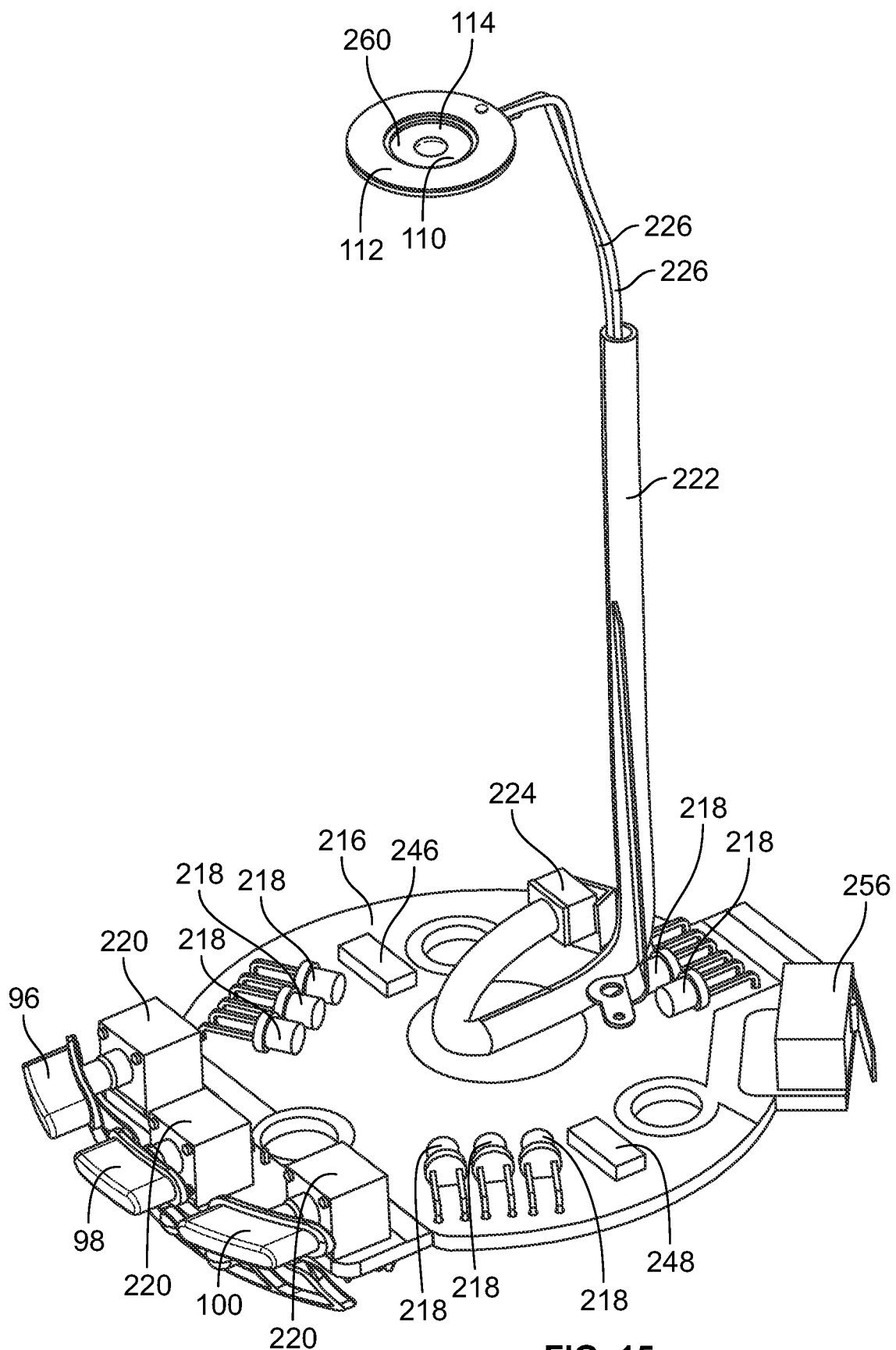
FIG. 15 is a front, top, and left isometric view of various electrical components of the volatile material dispenser of FIG. 1, including a piezoelectric element.

Referring to FIG. 15, the printed circuit board (PCB) 216, the wire guide 222 and the piezoelectric assembly 110 are shown in an isometric view. A controller 246 and a timer 248 are shown in schematic view along the PCB 216. The controller 246 may be a microcontroller, and may be disposed within or along the PCB 216. The controller 246 may also be a separate component that is electrically coupled with the PCB 216. The timer 248 may further be disposed within or along the PCB 216, or may be a separate component. The timer 248 is used to time when the dispenser 50 is activated, while the controller 246 is operable to receive instructions from the buttons 96, 98, 100 to activate the piezoelectric assembly 110, the timer 248, and/or the LEDs 218. As noted above, the PCB 216 is disposed between the base 56 and the platform 118, which are both removed from the view of FIG. 15 for clarity.

The LEDs 218, the buttons 96, 98, 100, the switches 220, and the wires 226 are shown clearly in the view of FIG. 15. A limit switch 256 is further shown, which provides a signal to the controller 246 that the shroud 54 has been secured to the base 56, and does not allow the dispenser 50 to be activated until the shroud 54 has been secured to the base 56. In some embodiments, there is no limit switch 256. The terminal 224 is further shown disposed along the PCB 216. Other electrical components, such as resistors, transistors, capacitors, processors, controllers, and relays may further be disposed along or within the PCB 216. In some embodiments, a plurality of batteries (not shown) may be enclosed within a casing (not shown) and may be electrically connected to the PCB 216 for providing electrical power to the PCB 216 and other electrical components of the dispenser 50.

Figure 16:
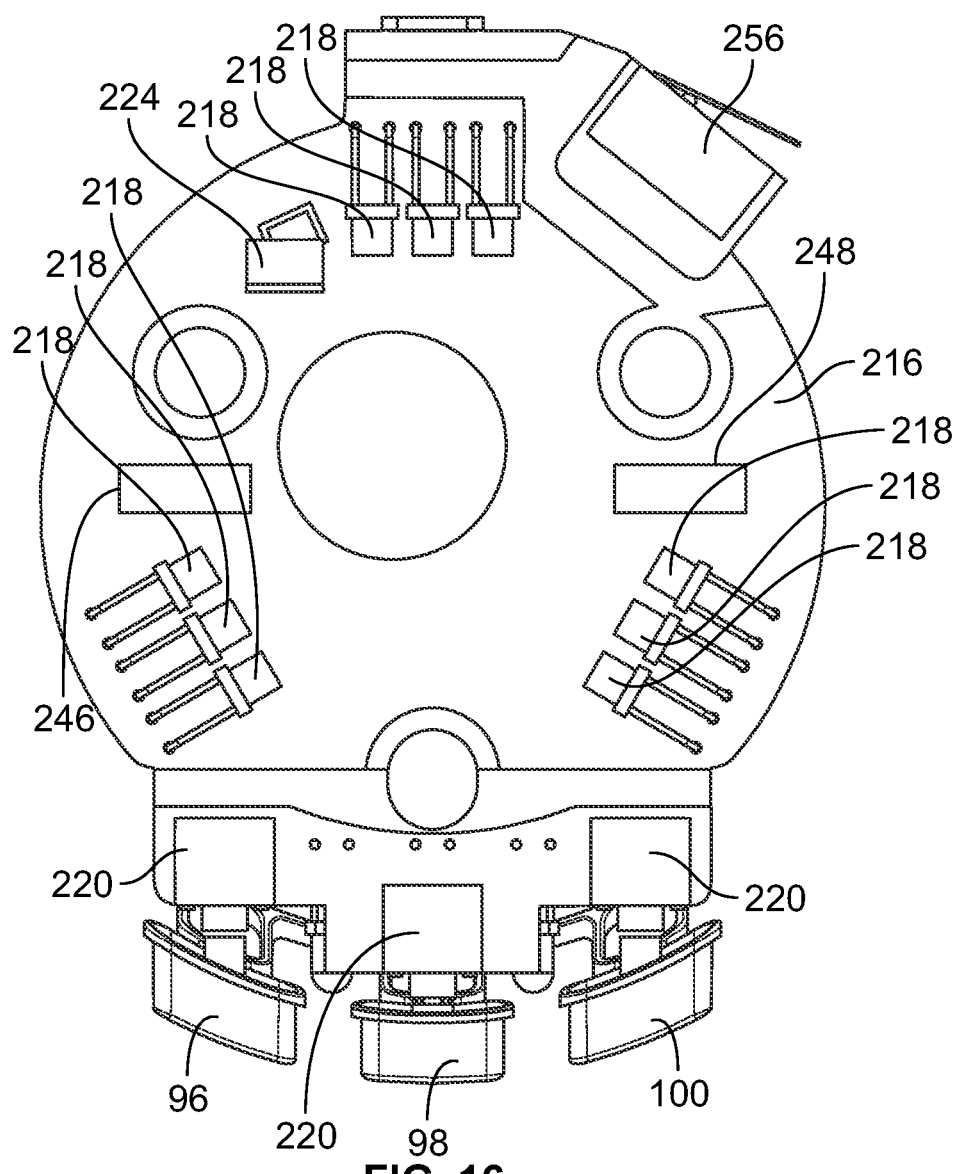
FIG. 16 is a top plan view of a printed circuit board and some of the electrical components shown in FIG. 15.

Referring to FIG. 16, a top view of the PCB 216 is shown with the wire guide 222 and the piezoelectric assembly 110 having been removed for clarity. The switches 220 are shown in greater detail, and are shown positioned adjacent each of the first button 96, second button 98, and third button 100. Further, three sets of three LEDs 218 each are shown in detail in a triangular configuration along the PCB 216. The different sets of LEDs 218 may emit different colored lights, or may emit the same color. Further, the LEDs 218 may have the same intensity or a different intensity from one another. The port 104 is further shown along the PCB 216 at an opposite end of the second button 98. The PCB 216 has a generally circular profile, however, the PCB 216 may have any profile that allows it to be securely retained within the profile of the shroud 54.

Figure 17:
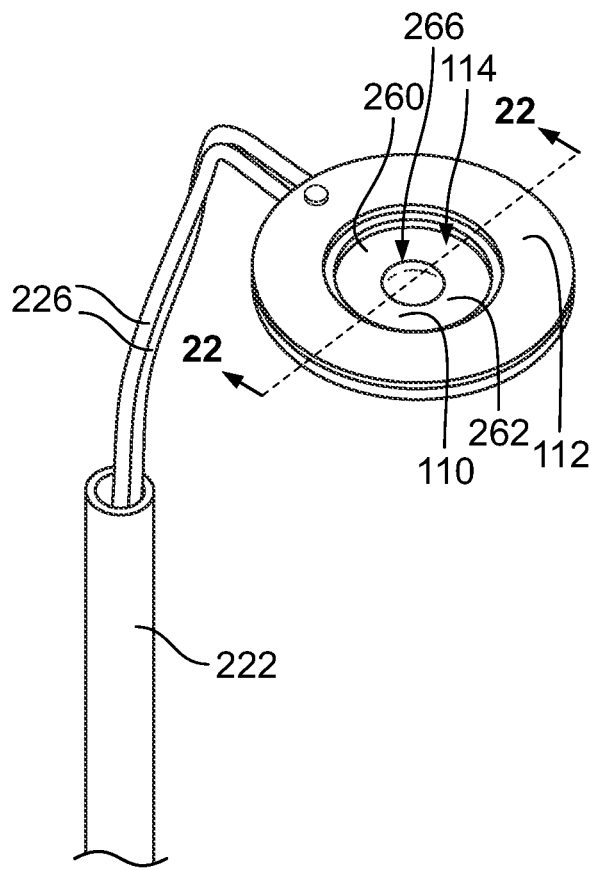
FIG. 17 is a front, top, and right isometric view of the piezoelectric element shown in FIG. 16.

Referring now to FIG. 17, the piezoelectric assembly 110 is shown in greater detail, along with the wires 226 and an upper end of the wire guide 222. The piezoelectric assembly 110 includes a piezoelectric plate 260 and the piezoelectric element 112 that circumscribes the periphery of an upper surface 262 of the piezoelectric plate 260. The piezoelectric plate may comprise stainless steel, which may be SUS 316L steel. When the piezoelectric element 112 is energized, the piezoelectric plate 260 is caused to expand and contract, thereby releasing a volatile into the surrounding environment. The piezoelectric plate 260 further includes a central dome 264 that is generally concave and circular in shape. The piezoelectric assembly 110 includes an apertured section 266, at least a portion of which extends along the central dome 264. In an illustrative embodiment, the apertured section 266 of the piezoelectric plate 260 includes a plurality of orifices 268 having a diameter or at least one width dimension of between about 3 microns and about 9 microns, or between about 5 and 7 microns, or about 6.5 microns. In other illustrative embodiments, the piezoelectric plate 260 includes a plurality of orifices having a diameter of between about 3 microns and about 5 microns.

Figure 18A:
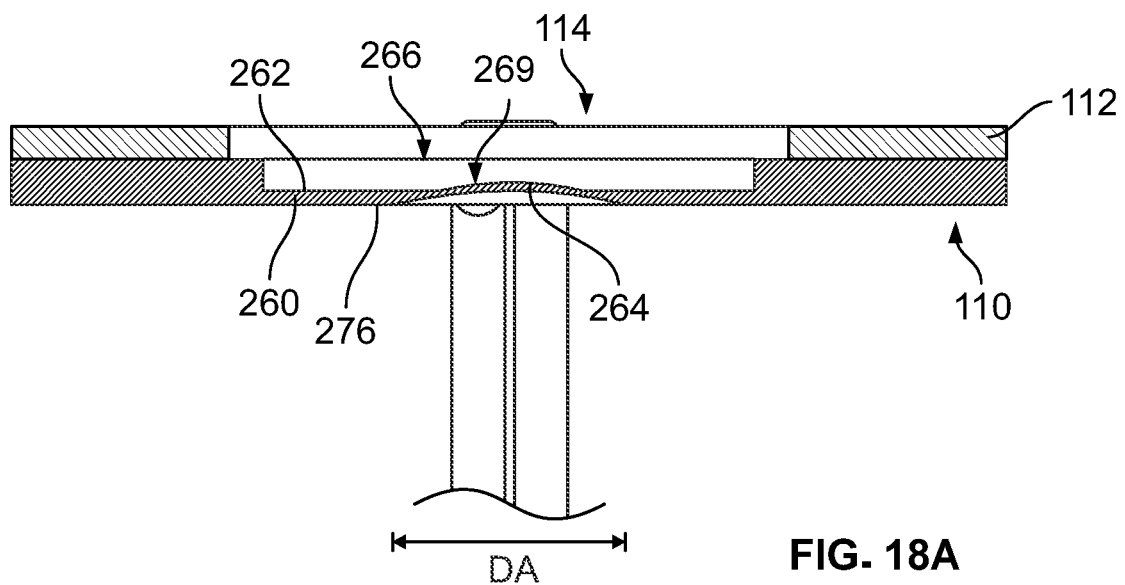
FIG. 18A is a cross-sectional view of the piezoelectric element taken through line 18-18 of FIG. 17.

Referring to FIGS. 17 and 18A, the piezoelectric assembly 110, when in use, is positioned adjacent the wick 188. In illustrative embodiments, the piezoelectric element 112 may be formed as a ring and may be made of ceramic. In alternative illustrative embodiments, the piezoelectric assembly 110 may be formed in any suitable shape and/or may be made of any suitable material having piezoelectric properties and which causes the material to change dimensionally in response to an applied electric field. Illustrative examples of suitable materials include, but are not limited to, lead zirconate titanate (PZT) or lead metaniobate (PN). While a particular piezoelectric element is described, any actuator may be utilized, for example, a piezoelectric vibrating mesh actuator, a piezoelectric standing wave actuator, a piezoelectric vibrating needle, or any other suitable piezoelectric actuator.

Figure 18B:
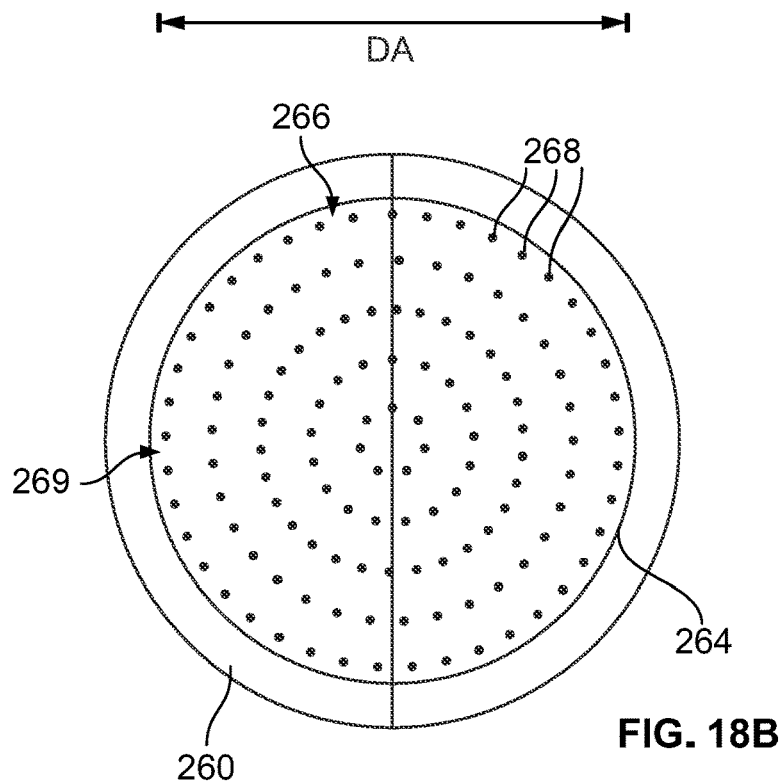
FIG. 18B is a schematic illustration of a circular-shaped array of apertures along the piezoelectric element of FIG. 17.
Figure 18C:
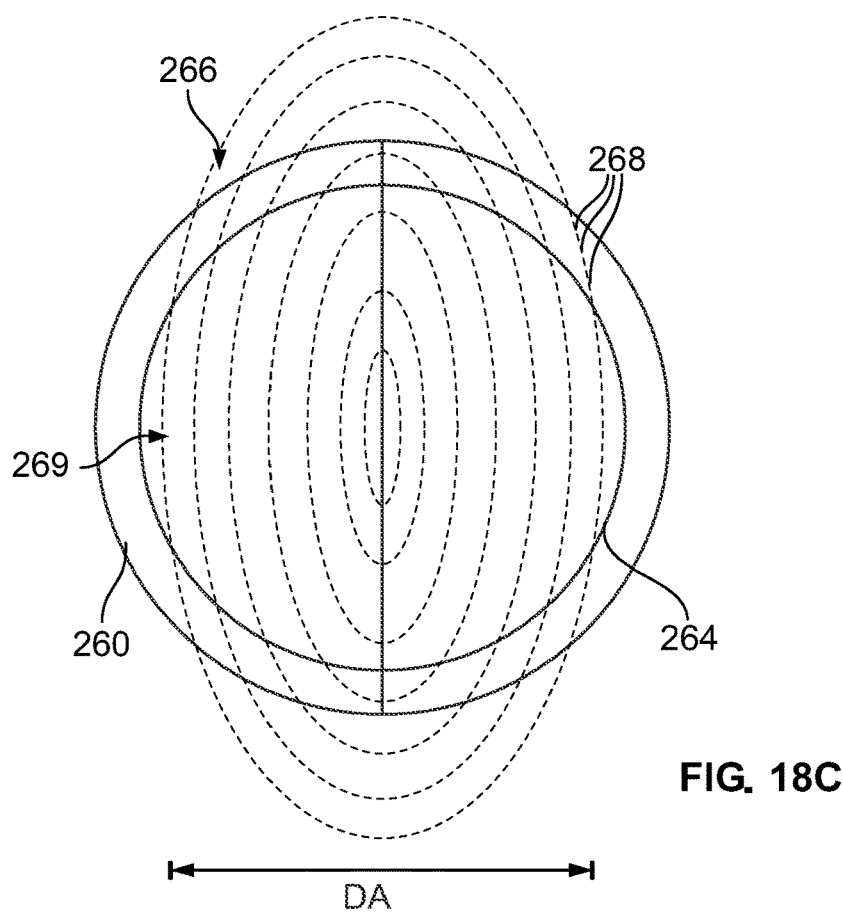
FIG. 18C is a schematic illustration of an oval-shaped array of apertures along the piezoelectric element of FIG. 17.

Referring to FIGS. 18B and 18C, the plurality of orifices 268 along the piezoelectric plate 260 may define an array 269 that is circular in nature. The array 269 of orifices may be defined along the entire dome 264, as shown in FIG. 266. The array 269 may alternatively be disposed along only a portion of the dome 264, or may extend beyond the dome 264, as depicted in FIG. 18C. The array 269 may have alternative configurations, and may be in the shape of a triangle, a square, an oval, or a polygon. Further, the orifices 268 may be in the shape of a circle (FIG. 18B), a rectangle or square (FIG. 18C), or another shape. It should be noted that the orifices 268 depicted in the schematic views of FIGS. 18B and 18C do not represent the actual size or actual number of the orifices 268, rather, the orifices 268 may define dimensions as noted herein.

In some embodiments, the array 269 has a diameter or at least one width dimension of between about 0.5 mm and about 10.0 mm, or between about 1.0 mm and about 9.0 mm, or between about 2.0 mm and about 8.0 mm, or between about 3.0 mm and about 7.0 mm. Referring again to FIG. 12, a wick diameter DW and an array diameter DA (see FIG. 18) may define a ratio of DA/DW of between about 1.0 and about 3.0. In some embodiments, the ratio is about 1.1. In some embodiments, the wick diameter DW is between about 3.0 mm and about 5.5 mm, or between about 3.5 mm and about 4.0 mm, or about 3.8 mm. In some embodiments, the array diameter DA is between about 3.0 mm and about 6.0 mm, or between about 4.0 mm and about 5.0 mm, or about 4.5 mm. The ratio of wick diameters may affect the accuracy and consistency of the plume of the volatile that is emitted by the dispenser 50. For example, having a ratio DW/DA of about 1.1 has been found to create a repeatable and accurate dispersal of volatile from the dispenser 50. In some embodiments the array 269 may comprise between about 100 and about 400 orifices, or between about 150 and about 350 orifices, or about 316 orifices, or about 200 orifices.

Referring now to FIGS. 19 and 20, detail views of the upper end of the stand assembly 116 are shown without and with a refill having been inserted therein, respectively. Referring to FIG. 19, the piezoelectric assembly 110 is shown in greater detail. In some embodiments, a soft material, such as loading foam, may be provided along an underside of the piezoelectric assembly 110. Additional materials may be provided along an underside of the piezoelectric assembly 110 to aid in accuracy or consistency of the plume of volatile generated when the dispenser 50 is activated. The additional materials may also be provided to enhance or reduce a dampening effect that could be caused by the spring 232, the wick 188, and/or the piezoelectric plate 260.

The top end 242 of the spring 232 is shown wrapped around the cylindrical wall 164, while the bottom end 244 of the spring 232 is shown in contact with and applying a force against the piezoelectric assembly 110. The chassis 122 further includes a piezo platform 270, which is unitary with the chassis 122 and defines a surface to which the piezoelectric assembly 110 is secured. The piezo platform 270 retains the piezoelectric assembly 110 in place, and prevents the piezoelectric assembly 110 from being displaced farther than the piezo platform 270. The piezo platform 270 is generally circular and includes an aperture 272 in a center thereof, which allows the distal end 204 of the wick 188 to engage in physical contact with the piezoelectric assembly 110 when inserted into the chassis 122. The spring 232 is positioned to provide an opposing force against the refill 52 when it has been inserted into the chassis 122. As noted below, when the wick 188 is engaged with the piezoelectric assembly 110, the spring 232 is compressed and the piezoelectric assembly 110 is displaced a distance X above the piezoelectric platform 270. This displacement is discussed in greater detail hereinafter below.

Referring to FIG. 20, the refill 52 is shown having been inserted into the manifold 126. Because the refill 52 has been inserted into the refill cavity 240 of the chassis 122, the spring 232 has been compressed, thus, the spring 232 is shown in a compressed configuration. Still referring to FIG. 20, the rim 152 of the refill 52 is also shown engaged with the catches 236 of the tabs 150, and the distal end 204 of the wick 188 is shown in physical contact with a lower surface 276 (see FIG. 18) of the piezoelectric assembly 110. The compression of the spring 232 shown in FIG. 20 is a result of the size and type of spring that is used in the dispenser 50, which may be chosen based upon a variety of factors, as discussed below. Other than the spring 232 having been compressed, the piezoelectric assembly 110 having been translated upward due to the force applied by the wick 232, and the catches 236 of the tabs 150 having been engaged with the rim 152 of the refill 52, no other elements of the manifold 126 are moved or manipulated when the refill 52 is inserted into the manifold 126. FIG. 20 shows the refill 52 in an operational state, where the dispenser 50 could be activated to disperse the volatile by providing an electrical pulse to the piezoelectric assembly 110.

In illustrative embodiments, and as noted above, an absorbent material (not shown) may be included between the wick 188 and the piezoelectric assembly 110. The absorbent material may be a felt pad and/or cotton wool. In other illustrative embodiments, the absorbent material may be formed of a velour pad, cotton cloth, chenille yarn, chenille fabric, polyester cloth, paper towel, synthetic cloth, synthetic nonwoven material, a cotton ball or swab, combinations thereof, or other suitable absorbent material(s). The absorbent material may be a component of the nebulizer assembly or may be attached or otherwise in communication with the wick 188 of the refill 52.

During operation, the piezoelectric assembly 110 is actuated, either continuously or intermittently, to dispense volatile material. More particularly, an oscillating electric field is applied to the piezoelectric element 112, which causes expansion and contraction of the piezoelectric plate 260 in a radial direction. The expansion and contraction causes the piezoelectric plate 260 to vibrate in an axial direction (along a longitudinal axis of the dispenser 50), forcing volatile material retained within the orifices of the piezoelectric plate 260 away from the piezoelectric assembly 110, through a channel 280 defined by the cylindrical wall 164, and through the chimney 78 of the shroud 54.

Figure 21:
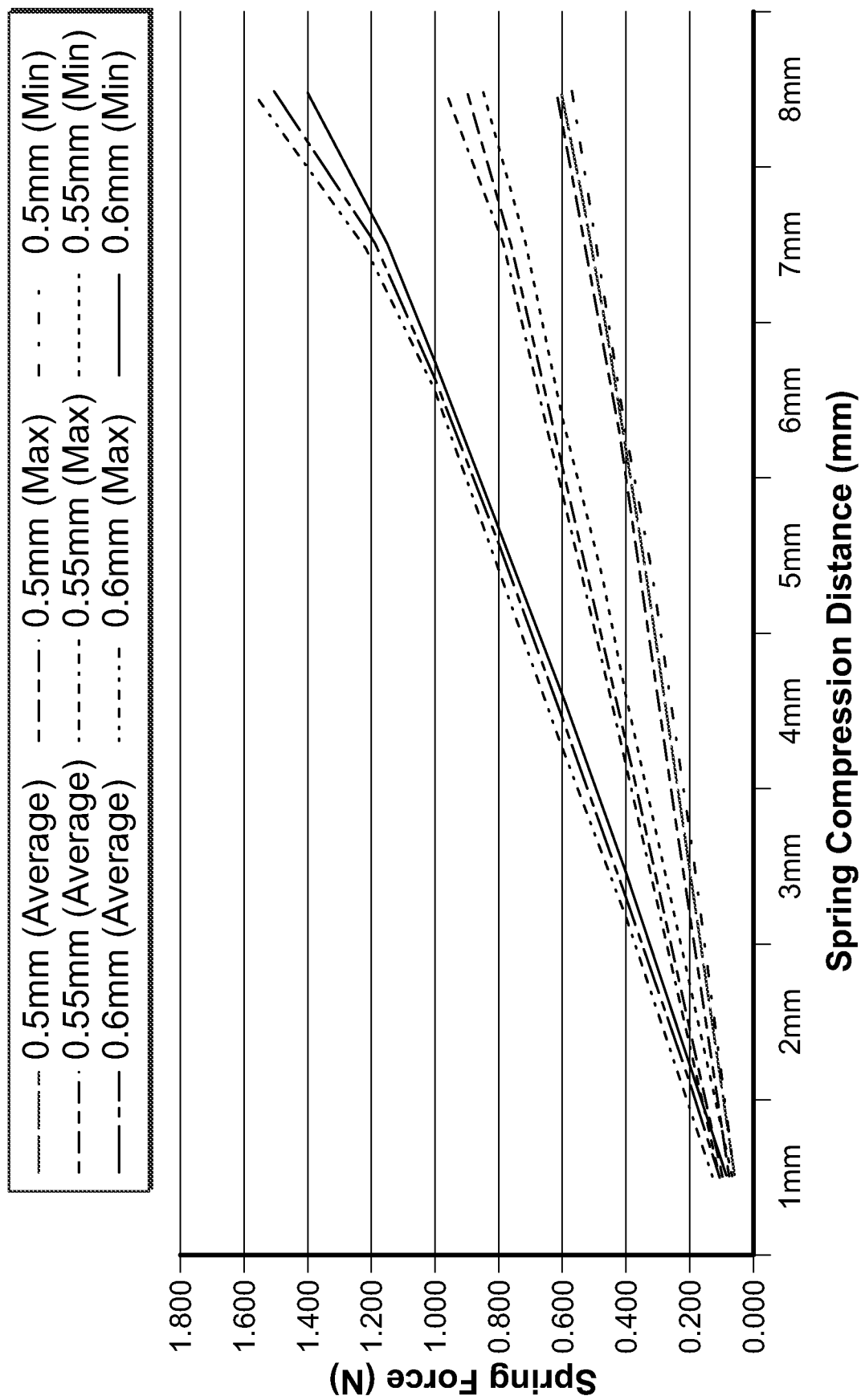
FIG. 21 is a line graph illustrating the results of various tests of springs having varying thicknesses.

Referring to the graph of FIG. 21, three separate groups of springs were tested as the spring 232 in the dispenser 50 described above, the results of which are illustrated in the figure. The three groups of springs comprise spring wires 226 having a diameter of 0.50 mm, a spring having a diameter of 0.55 mm, and a spring having a diameter of 0.60 mm. The graph illustrates a spring force measured in Newtons (N) against a spring compression distance measured in millimeters (mm). The spring compression distance is the distance X noted above, i.e., a distance between the piezoelectric platform 270 and the piezoelectric assembly 110 after the wick 188 causes the piezoelectric assembly 110 to be translated upward. The graph further illustrates a minimum, an average, and a maximum for each of the three springs. Testing involved iteratively compressing springs from 1.0 mm to 8.0 mm while recording the resulting force output (N). While the three different spring diameters, i.e., 0.50 mm, 0.55 mm, and 0.60 mm, achieved different results, the results suggest that at a compression of 7.0 mm, each of the three springs saw a non-linear increase in measured spring force.

In some embodiments, the spring 232 may have an uncompressed height of between about 7 mm and about 20 mm, or between about 10 mm and about 17 mm, or about 13 mm. Further, in some embodiments, the spring 232 may have between about 2 turns and about 10 turns, or between about 3 turns and about 7 turns, or about 4.5 turns. In a preferred embodiment, the spring 232 has a spring wire diameter of about 0.6 mm, an uncompressed height of about 13 mm, and comprises about 4.5 turns.

Figure 22:
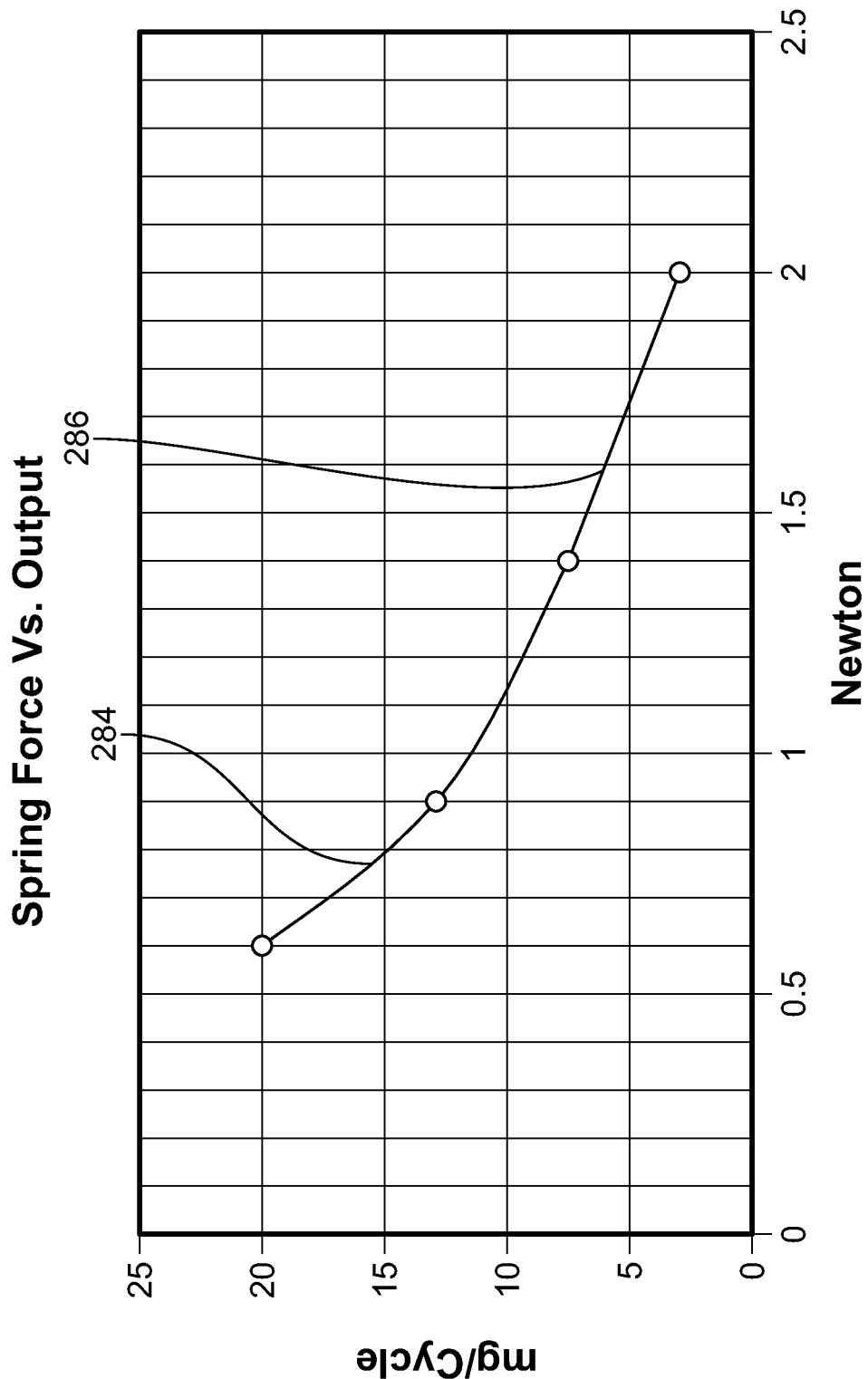
FIG. 22 is a line graph illustrating the results of a piezoelectric element and various tests comparing spring force against a resultant fragrance output.
Figure 23:
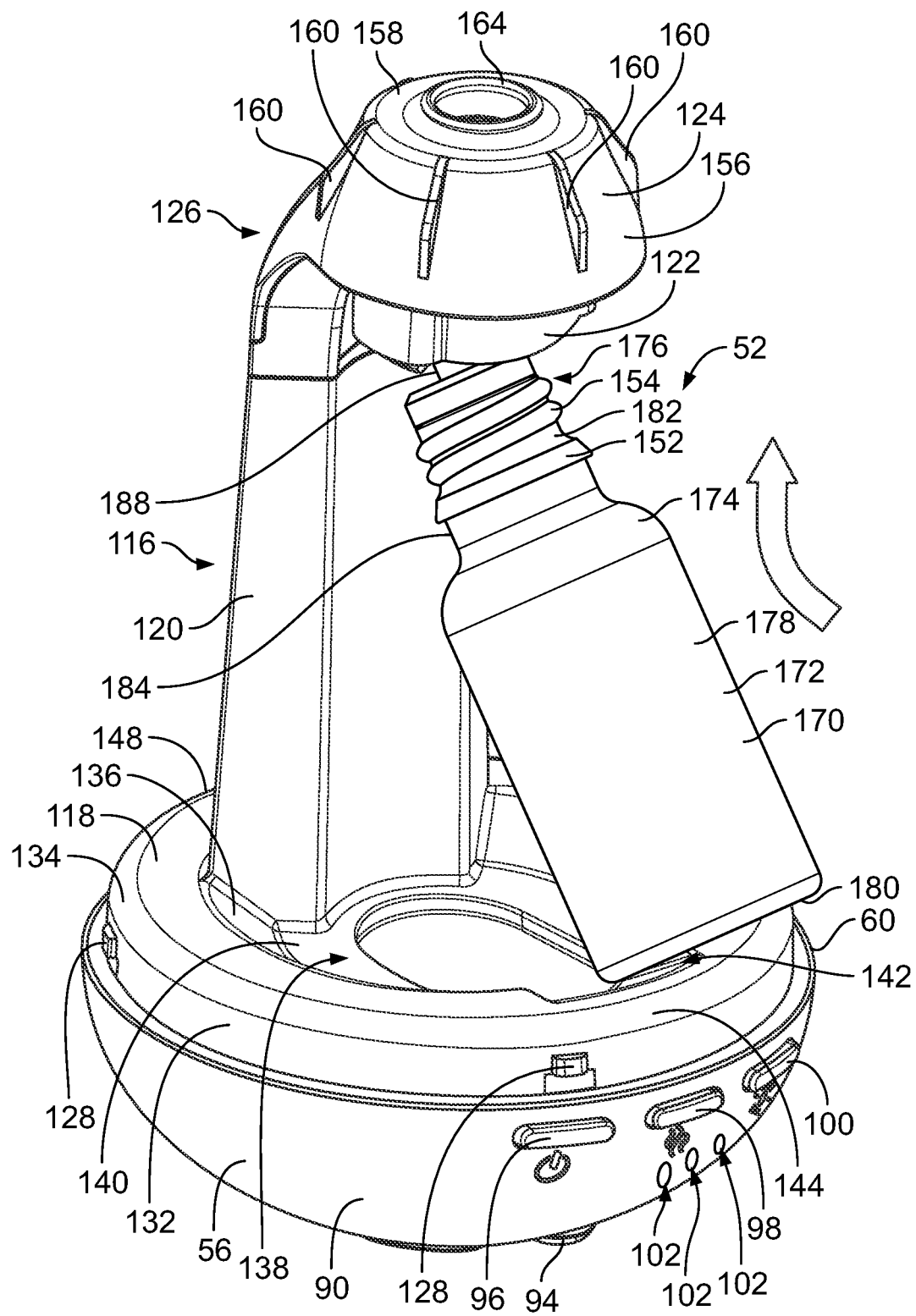
FIG. 23 is a front, right, and top view of the stand and base of FIG. 7 with the refill of FIG. 10 being inserted into a head cavity thereof.
Figure 24:
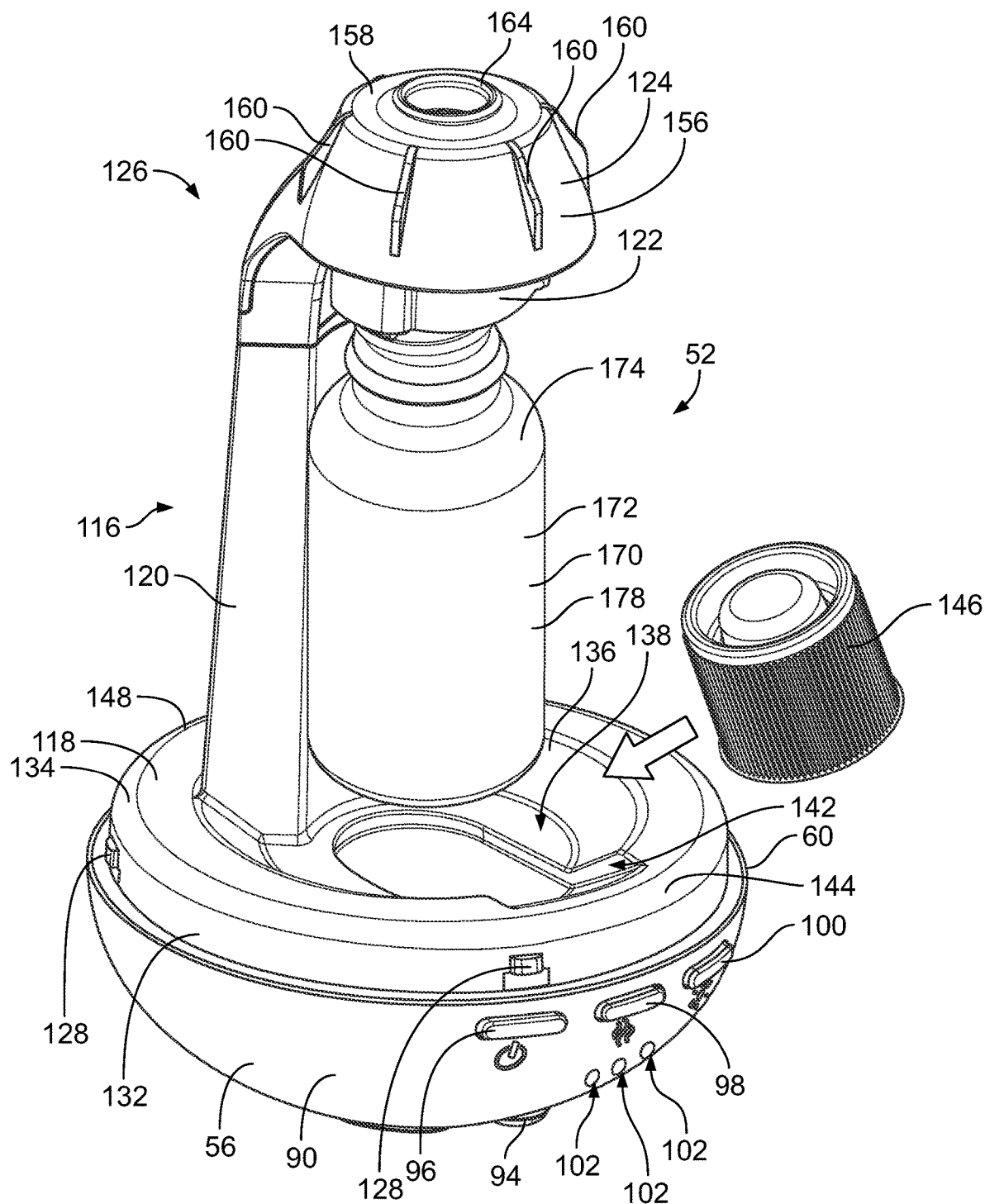
FIG. 24 is a front, right, and top view of the stand and base of FIG. 23 with the refill having been inserted into an engaged configuration.
Figure 25:
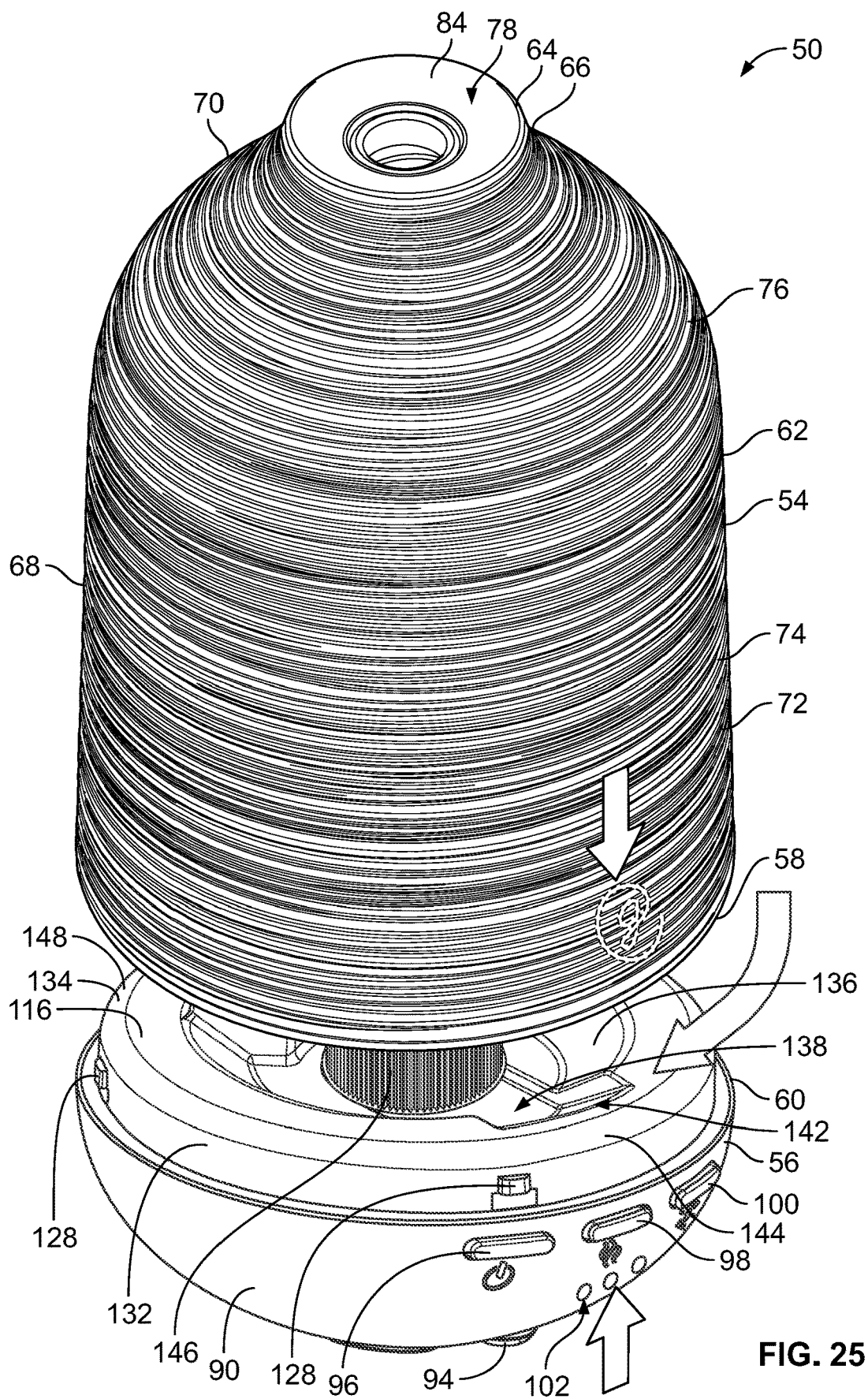
FIG. 25 is a front, right, and top view of the stand and base of FIG. 23 with a shroud being engaged with the base.

Referring now to the graph of FIG. 22, the spring force measured in Newtons (N) against a fragrance output measured in milligrams per cycle (mg/cycle) is shown. The graph illustrates results from the testing displayed in FIG. 21. The results of the tests suggest that the dispenser 50 emits a greater volume of fragrance when the springs induce lower compressive forces upon the piezoelectric plate 260. Fragrance emission patterns can be simplified into a first linear region 284 and a second linear region 286. The first region 284 occurs between 0.6 and 0.9 N and has an approximate slope of −25 mg/cycle/N. The second region 286 occurs between 0.9 and 2.0 N and has an approximate slope of −8.33 mg/cycle/N. The results suggest that the fragrance device emits a larger volume of fragrance when subjected to lower spring forces. As a result, depending on the desired range of outputs, a particular spring may be identified for use with the dispenser 50. To that end, the 0.50 mm or 0.55 mm spring would likely be utilized if one desired to achieve a fragrance output within the first linear region 284 and the 0.60 mm spring would likely be utilized if one desired to achieve a fragrance output within the second linear region 286.

Based on the testing, it was determined that having an upper wick 192 with a more pliable material causes less displacement of the spring 232 that applies a force against the piezoelectric assembly 110, which results in a more predictable dispersal of volatile. The variability of the dispensed plume is more predictable when operating within the linear region, while the variability of the release rate increases significantly when the force displacement of the spring 232 is non-linear. It has also been found that the amount of force that is applied by the spring 232 against the piezoelectric assembly 110 has a direct correlation with the release rate of the volatile. The lower the force, the more the piezoelectric assembly 110 can bounce within the channel 280.

Referring to FIGS. 23-25, a method of inserting the refill 52 into the stand assembly 116 and assembling the dispenser 50 are depicted. Referring to FIG. 23, the refill 52 is positioned with the head 176 thereof being inserted into the manifold 126. The lower wall 180 of the refill 52 is slid through the slot 142 of the platform 118 and the refill 52 is moved upward so that the head 176 is inserted into the manifold 126. Referring to FIG. 24, once the rim 152 of the refill 52 has been engaged with the catches 236 of the tabs 150, the refill 52 can be characterized as being secured within the manifold 126. The cap 146 of the refill 52 may be inserted into the well 138 to securely retain the cap 146 while the refill 52 is in use. Referring to FIG. 25, the shroud 54 is aligned with the base 56 and is rotated until the protrusions 128 along the base 56 engage with features along the underside 162 of the shroud 54. The shroud 54 may alternatively be engaged with the base 56 in another way. Once the shroud 54 has been coupled with the base 56, one end of a power cord (not shown) is plugged into the port 104 and the other end is plugged into a power source such as a power adapter, a laptop, or another low voltage outlet.

Still referring to FIG. 25, the first button 96 is a power button, the second button 98 is a fragrance strength button, and the third button 100 is a light button. The first button 96 may be pressed once to turn the dispenser on. The dispenser 50 will begin to dispense fragrance once the first button 96 has been depressed. The second button 98 and the third button 100 may be pressed to personalize the preference of the fragrance strength and/or the light scheme. During operation of the dispenser 50, it is desirable to have the wick 188 in contact with the piezoelectric plate 260. If the wick 188 is not in contact with the piezoelectric plate 260, especially in a water-based fragranced volatile material, the dispenser 50 may not function properly and/or may not emit volatile material at all.

Any of the embodiments described herein may be modified to include any of the structures or methodologies disclosed in connection with other embodiments. Further, although directional terminology, such as front, back, upper, lower, vertical, horizontal, etc. may be used throughout the present specification, it should be understood that such terms are not limiting and are only utilized herein to convey the orientation of different elements with respect to one another.

INDUSTRIAL APPLICABILITY

Dispensers are commonly used to dispense a variety of volatile materials such as air fresheners, deodorants, insecticides, germicides, perfumes, and the like, that are stored within refill containers. Piezoelectric engines allow the volatile materials to be volatilized and then distributed into an environment in order for the contents thereof to be released without human interaction, for example, continuously or according to a predetermined time schedule.

We claim:

1. A volatile material dispenser, comprising:

a base that houses a printed circuit board;

a stand assembly that is coupled with the base, the stand assembly including a platform, a stand that extends from the platform, and a manifold that extends from the stand, the manifold containing a circular piezoelectric element; and a shroud positioned on the base, the shroud defining a chimney that is centered along a longitudinal axis;

wherein the manifold includes an annular wall that extends from the manifold;

wherein a spring is disposed within the manifold and is coaxial with the annular wall, and wherein a top end of the spring is wrapped around the annular wall and a bottom end of the spring applies a force against the piezoelectric element.

2. The volatile material dispenser of claim 1, wherein the spring has a spring wire with a diameter of between about 0.50 mm and about 0.60 mm.

3. The volatile material dispenser of claim 2, wherein the diameter of the spring wire is about 0.55 mm.

4. The volatile material dispenser of claim 1, wherein the volatile material dispenser further comprises a fan.

5. The volatile material dispenser of claim 1, wherein the volatile material dispenser further comprises a refill that includes a wick, and wherein the refill is removably coupled with the manifold.

6. The volatile material dispenser of claim 5, wherein the spring causes a force to be exerted against the wick of the refill when the refill is inserted into the manifold.

7. The volatile material dispenser of claim 1, wherein the annular wall extends entirely around the longitudinal axis.

8. The volatile material dispenser of claim 1, wherein the manifold defines a refill cavity, and wherein a plurality of refill retaining ribs extend from the manifold into the refill cavity.

9. The volatile material dispenser of claim 1, wherein the manifold comprises a chassis and a crown that is snap fit to the chassis.

10. A volatile material dispenser, comprising:

a base that houses a printed circuit board, the base comprising a plurality of light emitting diodes;

a stand assembly that is coupled with the base, the stand assembly including a manifold, the manifold containing a piezoelectric assembly;

a shroud, the shroud defining a chimney that is centered along a longitudinal axis; and a refill comprising a wick, the refill being removably coupled with the manifold, wherein the refill is positioned entirely within the shroud when the refill is coupled with the manifold, wherein the manifold includes an annular wall that extends from the manifold, wherein a spring is disposed within the manifold and is coaxial with the annular wall, and wherein a top end of the spring is wrapped around the annular wall and a bottom end of the spring is in contact with the piezoelectric assembly.

11. The volatile material dispenser of claim 10, wherein the annular wall extends entirely around the longitudinal axis.

12. The volatile material dispenser of claim 10, wherein the base defines a sidewall, and wherein the base includes at least one button that projects from the sidewall.

13. The volatile material dispenser of claim 12, wherein the button is configured to activate the piezoelectric assembly.

14. The volatile material dispenser of claim 10, wherein the volatile material dispenser further comprises a fan.

* * * * *